(12) United States Patent
Brady-Kalnay

(10) Patent No.: US 9,415,122 B2
(45) Date of Patent: Aug. 16, 2016

(54) METHODS AND COMPOSITIONS FOR THE DETECTION OF CANCER CELLS

(71) Applicant: Case Western Reserve University, Cleveland, OH (US)

(72) Inventor: Susann Brady-Kalnay, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 282 days.

(21) Appl. No.: 13/938,968

(22) Filed: Jul. 10, 2013

(65) Prior Publication Data

US 2013/0287702 A1  Oct. 31, 2013

Related U.S. Application Data

(63) Continuation-in-part of application No. 13/059,025, filed as application No. PCT/US2009/053888 on Aug. 14, 2009, now Pat. No. 8,686,112.

(60) Provisional application No. 61/670,014, filed on Jul. 10, 2012, provisional application No. 61/733,062, filed on Dec. 4, 2012, provisional application No. 61/088,955, filed on Aug. 14, 2008.

(51) Int. Cl.
*C07K 14/00* (2006.01)
*A61K 49/00* (2006.01)

(52) U.S. Cl.
CPC ......... *A61K 49/0058* (2013.01); *A61K 49/0032* (2013.01); *A61K 49/0056* (2013.01)

(58) Field of Classification Search
CPC ... A61K 49/0056; C07K 14/00; C07K 14/435
USPC ...................................... 530/324, 325; 435/4
See application file for complete search history.

(56) References Cited

U.S. PATENT DOCUMENTS

| | | | | | |
|---|---|---|---|---|---|
| 5,604,094 A | * | 2/1997 | Schlessinger | ........ | C07K 14/705 435/196 |
| 6,160,090 A | * | 12/2000 | Schlessinger | ........ | C07K 14/705 530/350 |
| 2002/0146370 A1 | * | 10/2002 | Mueller | ........... | A61K 47/48646 424/1.69 |
| 2005/0260132 A1 | * | 11/2005 | Chin | ................. | A61K 47/48446 424/1.49 |

OTHER PUBLICATIONS

Krueger (Proc. Nat. Acad. Sci. U.S.A. 89:7417-7421 (1992).*

* cited by examiner

*Primary Examiner* — David Lukton
(74) *Attorney, Agent, or Firm* — Tarolli, Sundheim, Covell & Tummino LLP

(57) ABSTRACT

A molecular probe for use in detecting, monitoring, and/or imaging cancer cells and/or cancer cell metastasis, migration, dispersal, and/or invasion includes a targeting agent and a detectable moiety. The targeting agent specifically binds to and/or complexes with a proteolytically cleaved extracellular fragment of an immunoglobulin (Ig) superfamily cell adhesion molecule that is expressed by a cancer cell or another cell in the cancer cell microenvironment.

15 Claims, 11 Drawing Sheets

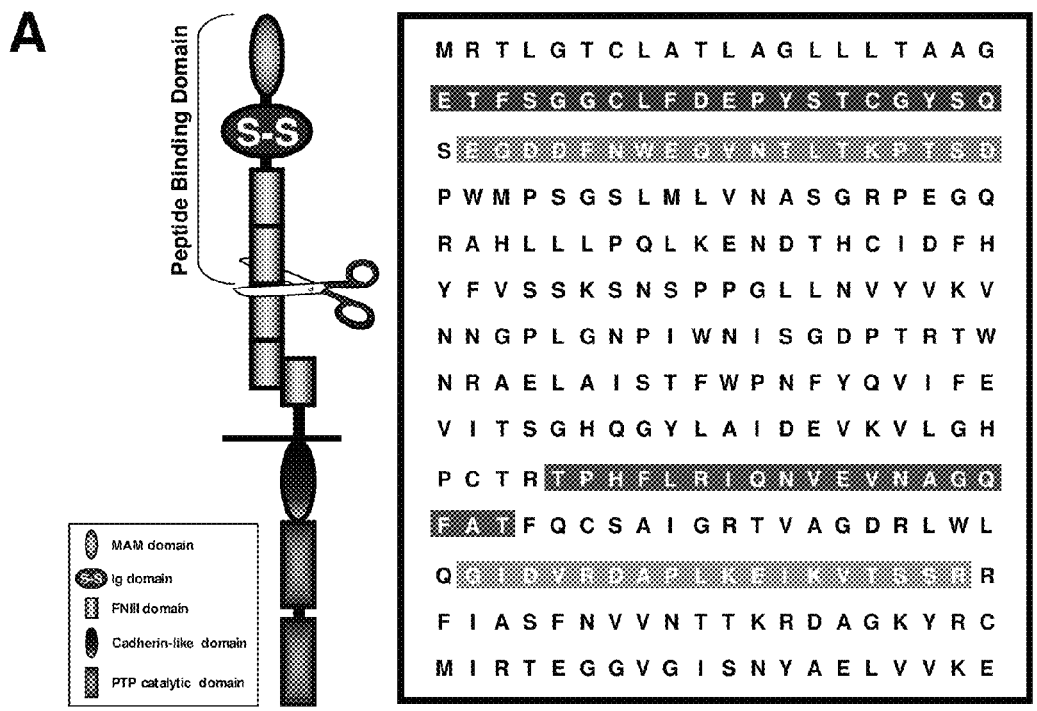
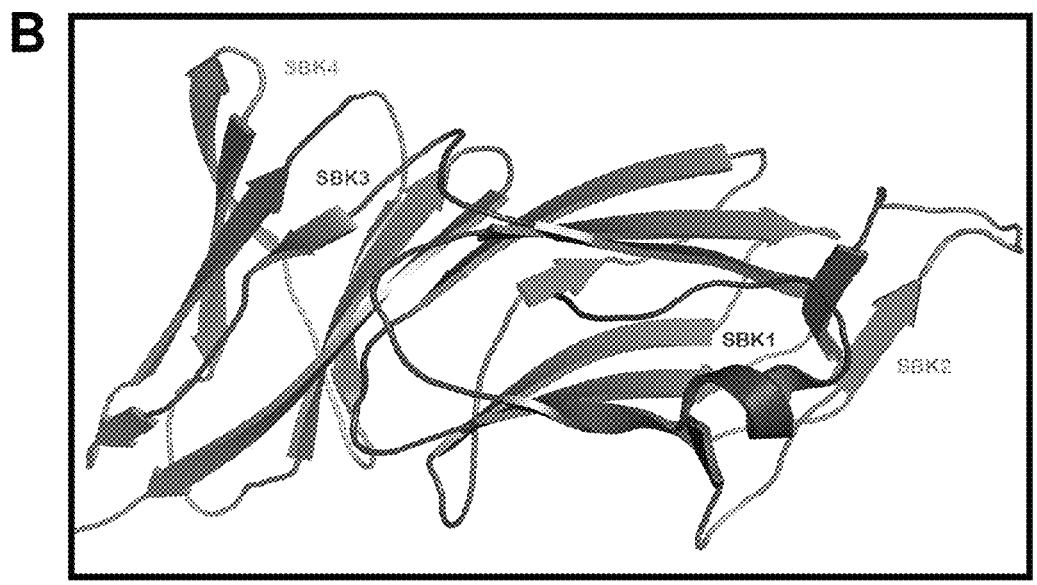
Figs. 1A-B

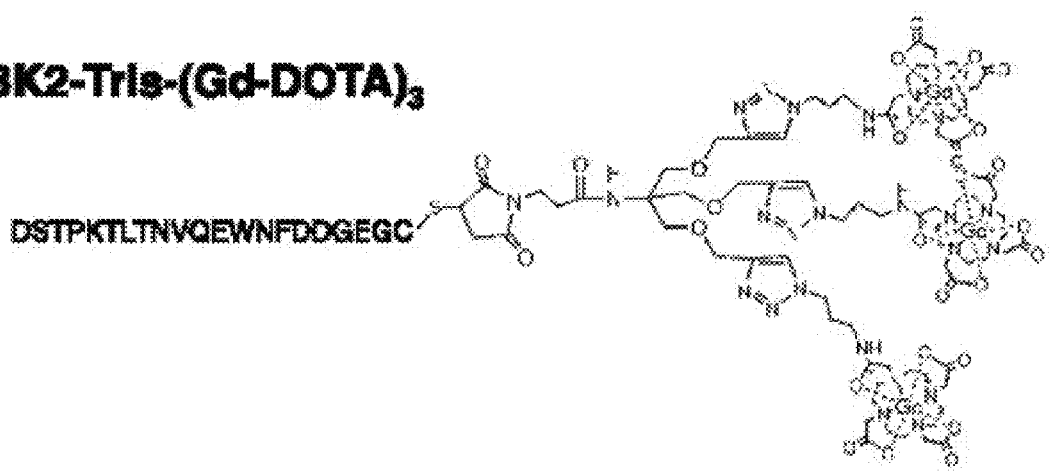
Fig. 9
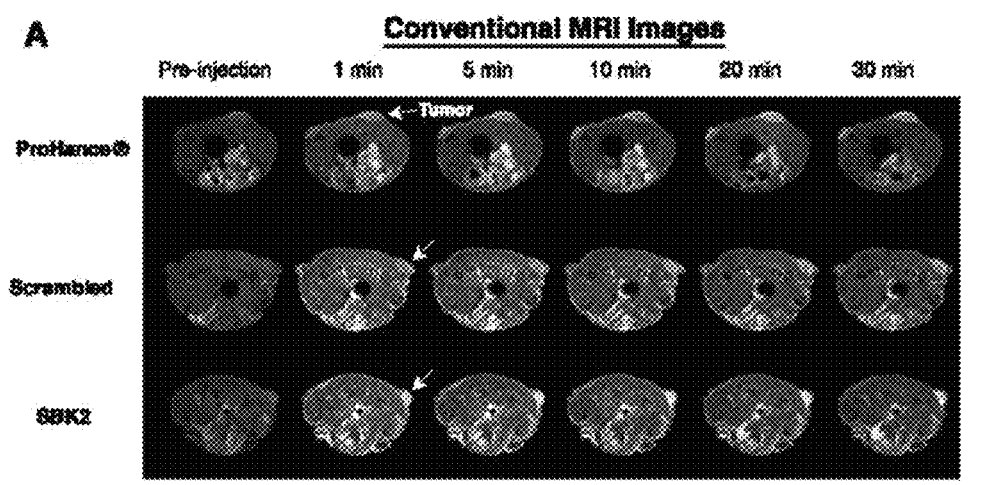
Figs. 10A-B

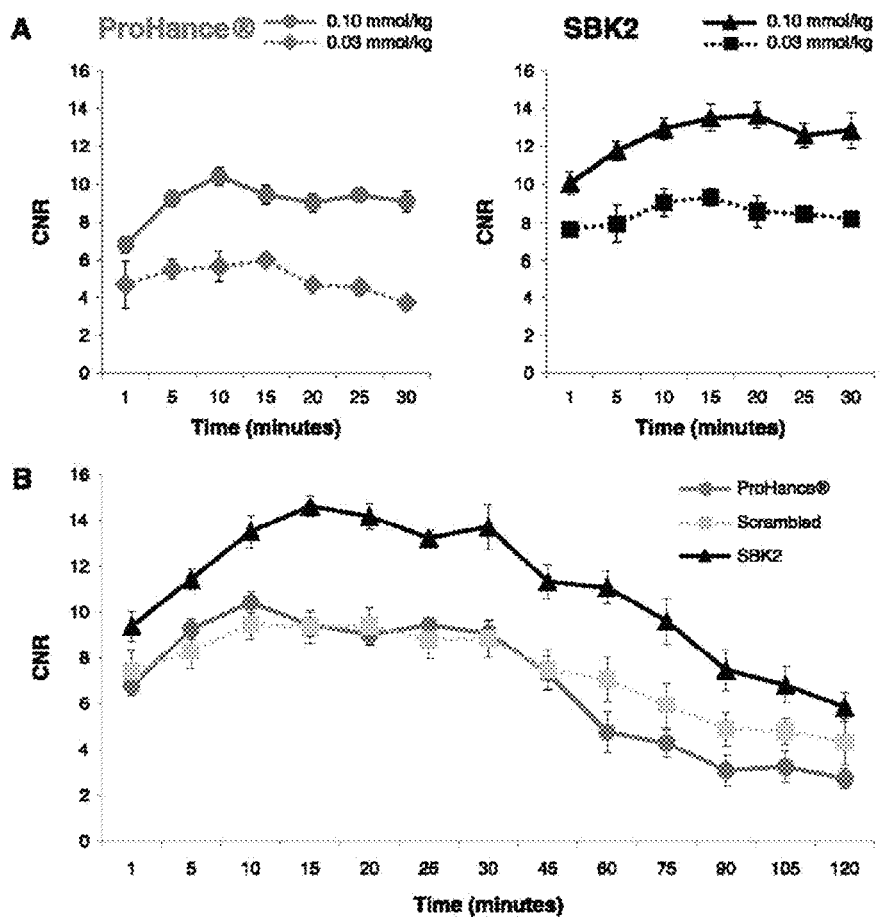
Figs. 13A-B
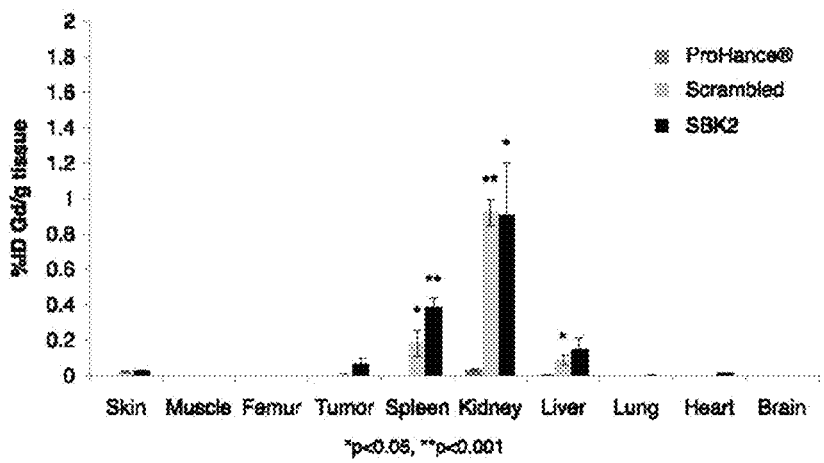
Fig. 14

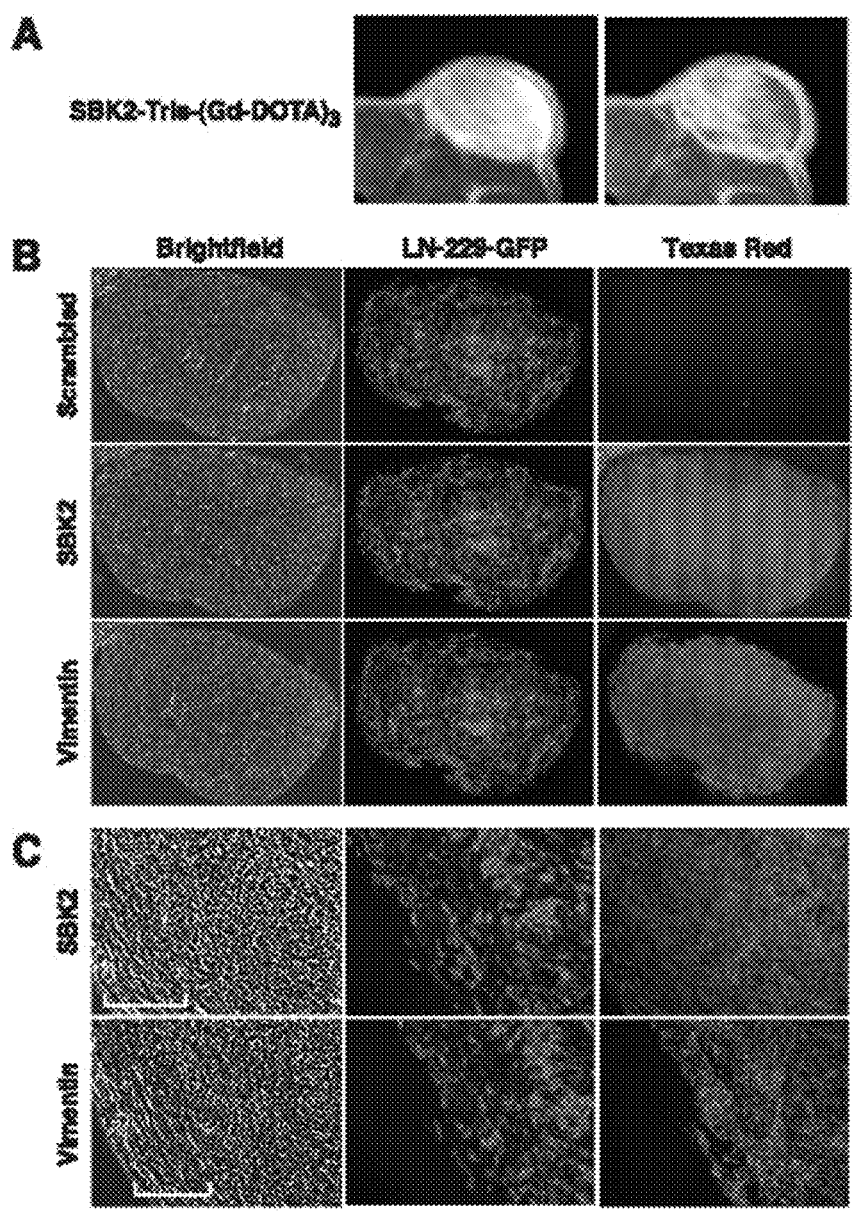
Figs. 15A-C

METHODS AND COMPOSITIONS FOR THE DETECTION OF CANCER CELLS

RELATED APPLICATION

This application claims priority of U.S. Provisional Application Ser. Nos. 61/670,014, filed Jul. 10, 2012 and 61/733,062, filed Dec. 4, 2012 and is a Continuation-in-part of U.S. patent application Ser. No. 13/059,025, filed Mar. 28, 2011, which is a National Phase Filing of PCT/US2009/053888, filed Aug. 14, 2009, which claims priority from U.S. Ser. No. 61/088,955, filed Aug. 14, 2008, the subject matter of which are incorporated herein by reference in their entirety.

BACKGROUND

Cancer detection and treatment are hindered by the inability to differentiate between cancer cells and normal cells. Better detection tools for cancer or tumor imaging are needed for earlier diagnosis of cancers. Molecular recognition of tumor cells would facilitate guided surgical resection. In order to improve surgical resection, targeted imaging tools must specifically label tumor cells, not only in the main tumor but also along the edge of the tumor and in the small tumor cell clusters that disperse throughout the body. Targeted imaging tools designed to label molecules that accumulate in the tumor microenvironment may also be advantageous as therapeutic targeting agents, as they can identify both the main tumor cell population and areas with infiltrating cells that contribute to tumor recurrence. The ability to directly target the tumor cell and/or its microenvironment would increase both the specificity and sensitivity of current treatments, therefore reducing non-specific side effects of chemotherapeutics that affect cells throughout the body.

SUMMARY

Embodiments described herein relate to molecular probes for use in detecting, monitoring, and/or imaging cancer cells and/or cancer cell metastasis, migration, dispersal, and/or invasion in a subject. The molecular probes include a targeting agent that specifically binds to and/or complexes with a proteolytically cleaved extracellular fragment of an immunoglobulin (Ig) superfamily cell adhesion molecule in the cancer cell microenvironment that is expressed by the cancer cell or another cell, such as a stem cell, endothelial cell, stromal cell or immune cell that supports survival of the cancer cell. The Ig superfamily cell adhesion molecule can include an extracellular homophilic or heterophilic binding portion, which can bind in homophilic or heterophilic fashion or engage in homophilic or heterophilic binding in a subject.

In some embodiments, the Ig superfamily cell adhesion molecule can include a cell surface receptor protein tyrosine phosphatase (PTP) type IIb, such as PTPμ or a PTPμ like molecule. The cancer cell can be, for example, a metastatic, migrating, dispersed, and/or invasive cancer cell, such as a metastatic, migrating, dispersed, and/or invasive brain cancer cell (e.g., glioma cell and, specifically, a glioblastoma multiforme (GBM) cell), lung cancer cell, breast cancer cell, prostate cancer cell, and/or melanoma.

In another embodiment, the extracellular fragment can have an amino acid sequence of SEQ ID NO: 2, and the targeting agent can specifically bind to and/or complex with SEQ ID NO: 2. In a further embodiment, the targeting agent can bind to homophilic binding domains or portion of the extracellular fragment, such as SEQ ID NO: 3, which comprises the MAM, Ig and first two FNIII repeat binding domain of PTPμ.

In yet another embodiment, the targeting agent can include a polypeptide having an amino acid sequence that has at least about 80%, about 90%, about 95%, about 96%, about 97%, about 98%, or about 99% sequence identity to about 10 to about 50 consecutive amino acids of the amino acid sequence of SEQ ID NO: 3. Examples of polypeptides having an amino acid sequence with an at least about 80% sequence identity to SEQ ID NO: 3 can be polypeptides having an amino acid sequence selected from the group consisting of SEQ ID NO: 4, SEQ ID NO: 5, SEQ ID NO: 6, and SEQ ID NO: 7.

In another embodiment, the molecular probe can include a detectable moiety that is linked to the targeting agent. The molecular probe can be detected in vivo by detecting, recognizing, or imaging the detectable moiety. The detectable moiety can be detected by at least one of gamma imaging, positron emission tomography (PET) imaging, computer tomography (CT) imaging, magnetic resonance imaging, near infrared imaging, or fluorescent imaging.

In still another embodiment, the molecular probe can be conjugated to a therapeutic agent (e.g., chemotherapeutic agent) that can treat the cancer cell. The therapeutic agent can be targeted to the cancer cells using the molecular probe.

Embodiments described herein also relate to methods of detecting, monitoring, and/or imaging cancer cells and/or cancer cell metastasis, migration, dispersal, and/or invasion in a subject. The method includes administering a molecular probe to the subject. The molecular probe includes a targeting agent that specifically binds to and/or complexes with a proteolytically cleaved extracellular fragment of an immunoglobulin (Ig) superfamily cell adhesion molecule in the cancer cell microenvironment that is expressed by the cancer cell or an endothelial cell that supports survival of the cancer cell. The Ig superfamily cell adhesion molecule can include an extracellular homophilic binding portion, which can bind in homophilic fashion or engage in homophilic binding in a subject. The molecular probe bound to and/or complexed with the proteolytically cleaved extracellular fragment of the Ig superfamily cell adhesion molecule is detected in the subject to detect and/or provide the location and/or distribution of the cancer cells in the subject.

In some embodiments, the Ig superfamily cell adhesion molecule can include a cell surface receptor protein tyrosine phosphatase (PTP) type IIb, such PTPμ or a PTPμ like molecule. The cancer cell can be, for example, a metastatic, migrating, dispersed, and/or invasive cancer cell, such as a metastatic, migrating, dispersed, and/or invasive brain cancer cell (e.g., glioma cell and, specifically, a glioblastoma multiforme (GBM) cell), lung cancer cell, breast cancer cell, prostate cancer cell, and/or melanoma.

In another embodiment, the molecular probe can include a detectable moiety that is linked to the targeting agent. The molecular probe can be detected in vivo by detecting, recognizing, or imaging the detectable moiety. The detectable moiety can be detected by at least one of gamma imaging, positron emission tomography (PET) imaging, computer tomography (CT) imaging, magnetic resonance imaging, near infrared imaging, or fluorescent imaging.

Embodiments described herein further relate to methods of determining and/or monitoring the efficacy of a cancer therapeutic and/or cancer therapy administered to a subject in need thereof. The method includes administering a molecular probe to the subject treated with the cancer therapeutic and/or cancer therapy. The molecular probe includes a targeting agent that specifically binds to and/or complexes with a proteolytically cleaved extracellular fragment of an immunoglobulin (Ig) superfamily cell adhesion molecule in the cancer cell microenvironment that is expressed by the cancer cell or an endothelial cell that supports survival of the cancer cell. The Ig superfamily cell adhesion molecule can include an extracellular homophilic binding portion, which can bind in homophilic fashion or engage in homophilic binding in a subject. The molecular probe bound to and/or complexed with the proteolytically cleaved extracellular fragment of the Ig superfamily cell adhesion molecule is detected in the subject to detect and/or provide the location and/or distribution of the cancer cells in the subject. The location and/or distribution of the cancer cells in the subject can then be compared to a control to determine the efficacy of the cancer therapeutic and/or cancer therapy.

In some embodiments, the control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the molecular probe to the subject and detecting the molecular probe bound to and/or complexed with cancer cells in the subject prior to administration of the cancer therapeutic and/or cancer therapy.

In some embodiment, the molecular probe can include a detectable moiety that is linked to the targeting agent. The molecular probe can be detected in vivo by detecting, recognizing, or imaging the detectable moiety. The detectable moiety can be detected by at least one of gamma imaging, positron emission tomography (PET) imaging, computer tomography (CT) imaging, magnetic resonance imaging, near infrared imaging, or fluorescent imaging.

BRIEF DESCRIPTION OF THE DRAWINGS

FIGS. 1(A-B) illustrate: (A) A schematic view of a PTPµ structure and targeting polypeptide probe sequences. PTPµ is a transmembrane protein that mediates efficient cell-cell adhesion via the MAM domain, Ig domain and FNIII repeats within its extracellular segments. The scissors indicate the approximate site where PTPµ is cleaved to generate a 55 kDa N-terminal fragment. The sequence is shown for the PTPµ MAM and Ig domains (i.e., SEQ ID NO: 2). The highlighted regions indicate the sequences used to generate PTPµ peptide probes (i.e., SBK1 (SEQ ID NO: 4), SBK2 (SEQ ID NO: 5), SBK3 (SEQ ID NO: 6), and SBK4 (SEQ ID NO: 7). (B) Crystal structure of the Ig and MAM domains of PTPµ (PDB ID: 2V5Y). SBK1 (SEQ ID NO: 4) and SBK2 (SEQ ID NO: 5) were derived from the N-terminal MAM domain while SBK3 (SEQ ID NO: 6) and SBK4 (SEQ ID NO: 7) were from the Ig domain.

FIG. 9 illustrates the structure of the targeted contrast agent SBK2 (SEQ ID NO: 5)-Tris-(Gd-DOTA)$_3$.

FIGS. 10(A-B) illustrate: (A) Representative T 1-weighted axial 2D gradient images of LN-229 flank tumor-bearing mice before (pre-injection) and at 1, 5, 10, 20, and 30 minutes after the intravenous injection of ProHance, scrambled Tris-(Gd-DOTA)$_3$, or SBK2-Tris-(Gd-DOTA)$_3$ at 0.1 mmol Gd/kg [n=7 tumors from four mice for ProHance; n=11 tumors from six mice for both SBK2-Tris-(Gd-DOTA)$_3$ and SBK2-Tris-(Gd-DOTA)$_3$]. White arrow indicates tumor. (B) Axial 2D gradient images shown in A with heat map overlays on the tumor to indicate contrast intensity. Key indicates relative level of contrast intensity with red being the most intense.

FIGS. 13(A-B) illustrate: (A) Dose-response plots of LN-229 flank tumor contrast-to-noise ratio (CNR) with ProHance or SBK2-Tris-(Gd-DOTA)$_3$ administered at 0.03 mmol Gd/kg (n=3 per condition) or 0.1 mmol Gd/kg [n=7 tumors from four mice for ProHance; n=11 tumors from six mice for SBK2-Tris-(Gd-DOTA)$_3$]. (B) Plots comparing LN-229 flank tumor CNR over a 2-hour period following intravenous administration of ProHance, scrambled Tris-(Gd-DOTA)$_3$, or SBK2-Tris-(Gd-DOTA)$_3$ contrast agents (0.1 mmol Gd/kg; n=6 tumors from three mice per condition). Data shown as means±SEM.

FIG. 14 illustrates a histrogram showing the biodistribution of gadolinium in the major organs and tissues of mice at 7 days after intravenous administration of ProHance, scrambled Tris-(Gd-DOTA)$_3$, or SBK2-Tris-(Gd-DOTA)$_3$ contrast agents at a dose of 0.1 mmol Gd/kg in nu/nu athymic mice bearing LN-229 flank tumors (n=3 mice per condition). Data shown as means±SEM (*P<0.05, **P<0.001 compared to ProHance).

FIGS. 15(A-C) illustrate: (A) Zoomed grayscale and heat map images by MRI following administration of SBK2-Tris-(Gd-DOTA)$_3$. (B) Images showing the corresponding histologic sections labeled with SBK2-Texas Red or scrambled Texas Red probes, or anti-human vimentin antibody. Images were acquired across the entire tissue using bright-field and fluorescence optics for fluorescein (GFP) and Texas Red (probe and antibody). The resultant images were tiled and flattened to form a single composite image using Metamorph software. Anti-human vimentin antibody recognizes the human glioma tumor cells. There is co-registration of the GFP-positive and vimentin-positive cells in these tumors. (C) Zoomed images of the histologic sections are shown for each type of staining. The bracketed region in C indicates the encapsulated region surrounding the tumor.

DETAILED DESCRIPTION

Figure 2:
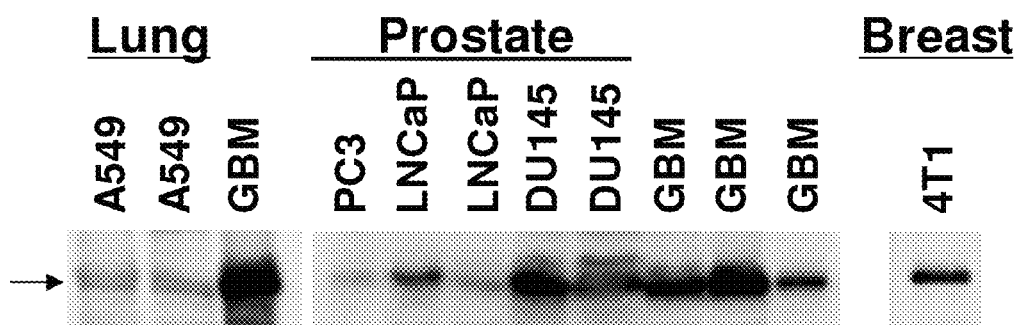
FIG. 2 illustrates an immuno-blot showing tumor cell line Xenografts generate PTPµ extracellular fragment in lung (A549), prostate, (PC3, LNCaP, DU145) glioblastoma (GBM) and breast tumor (4T1) cells.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "agent" is used herein to denote a chemical compound, a mixture of chemical compounds, a biological macromolecule, or an extract made from biological materials.

The terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The term "gene" or "recombinant gene" refers to a nucleic acid comprising an open reading frame encoding a polypeptide, including both exon and (optionally) intron sequences.

The term "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The term "monoclonal" refers to an antibody that specifically binds to a sequence of amino acid and/or a specific epitope of an antigen.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The term "polyclonal" refers to a combination of antibodies that recognize multiple epitope sites on a single antigen.

The terms "polynucleotide sequence" and "nucleotide sequence" are also used interchangeably herein.

"Recombinant," as used herein, means that a protein is derived from a prokaryotic or eukaryotic expression system.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The term "wild type" refers to the naturally-occurring polynucleotide sequence encoding a protein, or a portion thereof, or protein sequence, or portion thereof, respectively, as it normally exists in vivo.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to molecular probes for use in detecting, monitoring, and/or imaging cancer cells and/or cancer cell metastasis, migration, dispersal, and/or invasion in a subject, methods of detecting, monitoring, and/or imaging cancer cells and/or cancer cell metastasis, migration, dispersal, and/or invasion in a subject, and methods of determining and/or monitoring the efficacy of a cancer therapeutic and/or cancer therapy administered to a subject in need thereof.

The molecular probes described herein include a targeting agent that specifically binds to and/or complexes with a proteolytically cleaved extracellular fragment of an immunoglobulin (Ig) superfamily cell adhesion molecule in the cancer cell microenvironment that is expressed by the cancer cell or an endothelial cell, which supports survival of the cancer cell. The Ig superfamily cell adhesion molecule can include an extracellular homophilic binding portion, which can bind in homophilic fashion or engage in homophilic binding in a subject.

The molecular probes can be administered systemically to a subject and readily target cancer cells associated with proteolytically cleaved extracellular fragment of the immunoglobulin (Ig) superfamily cell adhesion molecule, such as metastatic, migrating, dispersed, and/or invasive cancer cells. In some embodiments, the molecular probe after systemic administration can cross the blood brain barrier to define cancer cell location, distribution, metastases, dispersions, migrations, and/or invasion as well as tumor cell margins in the subject.

It was found that metastic cancer cell migration or cancer cell dispersal can occur along characteristic pathways of anatomical structures (e.g., brain), which are rich in cell adhesion molecules (CAMs) and extracellular matrix molecules (ECM) that are permissive substrates for cell migration. In some instances, cancer cell dispersal requires the production of proteolytic enzymes, which gives the cell the ability to move through its environment. For example, metastatic cancer cells can overexpress growth factor receptor protein tyrosine kinases and their ligands, which is an important prerequisite for tumor growth and dispersal. The activity of the receptor tyrosine kinases is normally kept in check by the opposing activity of protein tyrosine phosphatases, such as receptor protein tyrosine phosphatases (RPTPs) (e.g., PTPμ), which are thought to be important regulators of adhesion-dependent signals.

RPTP type IIb cell adhesion molecules can include an extracellular segment that engages in homophilic binding. For example, the extracellular fragment of PTPμ, which is expressed by cancer cells, such as glioblastoma (GBM) cells, lung cancer cells, breast cancer cells, prostate cancer cells, and/or melanoma cells, can include a MAM domain, an immunoglobulin (Ig) domain and four fibronectin type III (FNIII) repeats. PTPμ binds homophilically (i.e., the "ligand" for PTPμ is an identical PTPμ molecule on an adjacent cell) and can mediate cell-cell aggregation. The Ig domain of PTPμ is responsible for promoting homophilic interactions and proper cell surface localization. The MAM domain also plays an important role in cell adhesion and sorting. The first two FNIII repeats contribute to efficient cell adhesion. When expressed on the cell surface, PTPμ mediates cell-cell adhesion and transduces signals in response to adhesion that may regulate contact inhibition of growth and/or movement.

In at least some human cancer cells and endothelial cells, which support cancer cell survival, the Ig superfamily cell adhesion molecules that are expressed and include an extracellular segment, are proteolytically cleaved and found to associate with or localize to the cancer cell microenvironment. It was found that molecular probes, that can specifically bind to and/or complex with these proteolytically cleaved extracellular fragments or segments can be used to detect these cancer cells as well as cancer cell metastasis, migration, dispersal, and/or invasion in a subject and define cancer metastases and invasive tumor margins in a subject.

Figure 3:
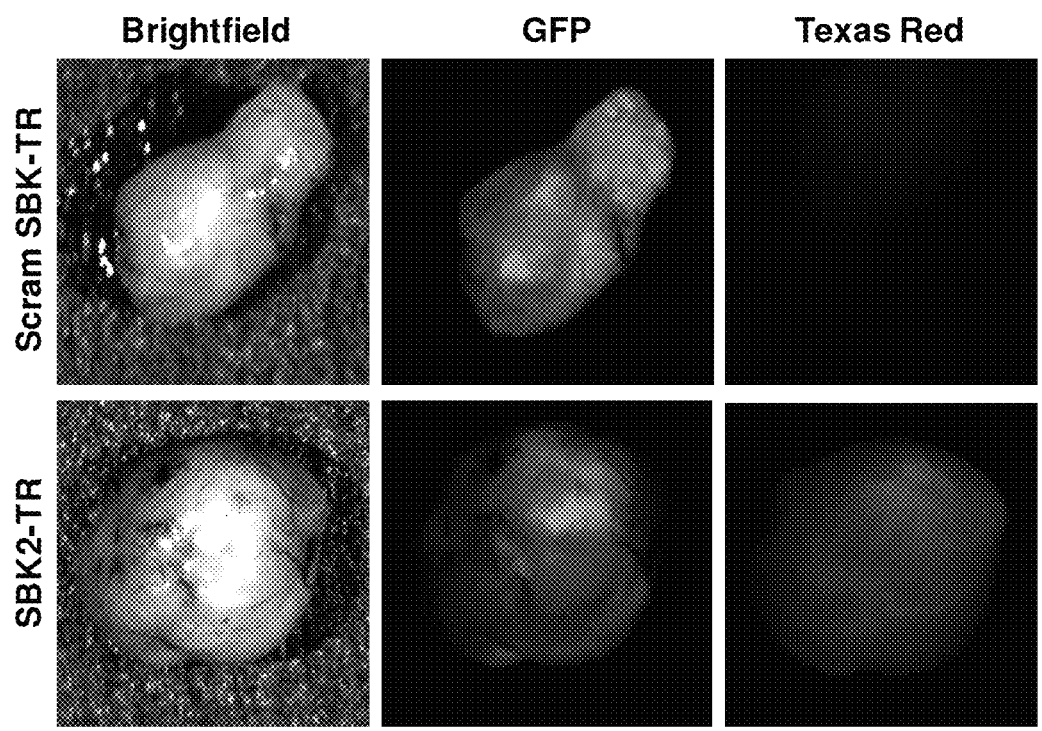
FIG. 3 illustrates images showing prostate tumors recognized by the PTPµ probe (SBK2-TR) (Texas Red).

By way of example, it was determined that proteolytically cleaved PTPμ extracellular fragments are common to high-grade glioblastomas, lung cancer cells, breast cancer cells, prostate cancer cells, and melanoma cells (See for example, FIGS. 2 and 3). Molecular probes to the PTPμ fragment were shown to clearly demarcate the tumor cells in tissue sections and the PTPμ extracellular fragment is present in human tumor "edge" samples, suggesting that the molecular probe can be used as diagnostic tools for molecular imaging of metastatic, dispersive, migrating, or invading cancers or the tumor margin. Systemic introduction of molecular probe as described herein resulted in rapid and specific labeling of the flank tumors within minutes. Labeling occurred primarily within the tumor, however a gradient of molecular probe at the tumor margin was also observed. There is also a signal amplification effect as extracellular fragments accumulate over time.

The molecular probes described herein can therefore be used in a method of detecting cancer cells and/or cancer cell metastasis, migration, dispersal, and/or invasion by administering to a subject a molecular probe that binds to and/or complexes with the proteolytically cleaved extracellular fragment of the Ig superfamily cell adhesion molecule in the cancer cell or tumor cell microenvironment and detecting the molecular probe bound to and/or complexed with the proteolytically cleaved extracellular fragment of the Ig superfamily cell adhesion molecule in the cancer cell or tumor cell microenvironment.

In one example, the Ig superfamily cell adhesion molecule includes RPTP type IIb cell adhesion molecules. In another example, Ig superfamily cell adhesion molecules can include RPTPs of the PTPμ-like subfamily, such as PTPμ, PTPκ, PTPρ, and PCP-2 (also called PTPλ). PTPμ-like RPTPs include a MAM (Meprin/A5-protein/PTPμ) domain, an Ig domain, and FNIII repeats. PTPμ can have the amino acid sequence of SEQ ID NO: 1, which is identified by Genbank Accession No. AAI51843.1. It will be appreciated that the PTPμ gene can generate splice variants such that the amino acid sequence of PTPμ can differ from SEQ ID NO: 1. In some embodiments, PTPμ can have an amino acid sequence identified by Genbank Accession No. AAH51651.1 and Genbank Accession No. AAH40543.1.

Cancer cells and/or endothelial cells, which support cancer cell survival, that express an Ig superfamily cell adhesion molecule and that can be proteolytically cleaved to produce a detectable extracellular fragment can include, for example, metastic or motile cancer cells and/or other cells in the tumor microenvironment, such as stem cells, endothelial cells, stromal cells and immune cells that promote their survival. In some embodiments, the cancer cells can include glioma cells, lung cancer cells, breast cancer cells, prostate cancer cells, and melanoma cells, such as invasive, dispersive, motile or metastic cancer cells can include glioma cells, lung cancer cells, breast cancer cells, prostate cancer cells, and melanoma cells. It will be appreciated that other cancer cells and/or endothelial cells, which support cancer cell survival, that express an Ig superfamily cell adhesion molecule and that can be proteolytically cleaved to produce a detectable extracellular fragment can identified or determined by, for example, using immunoassays that detect the Ig superfamily cell adhesion molecule expressed by the cancer cells or endothelial cells.

The molecular probe that is used to detect the extracellular fragment of the proteolytically cleaved extracellular fragment of the Ig superfamily cell adhesion molecule that engages in homophilic binding can include a targeting agent that specifically binds to and/or complexes with the proteolytically cleaved extracellular fragment of the Ig superfamily cell adhesion molecule of the cancer cell. The targeting agent can include a targeting small molecule, polypeptide, or antibody or a fragment of an antibody, such as an Fc fused to the extracellular segment of an Ig superfamily cell adhesion molecule (Fc chimera) that binds to and/or complexes with the proteolytically cleaved extracellular fragment of the Ig superfamily cell adhesion molecule and that can readily be administered to the subject using, for example, parenteral or systemic administration techniques (e.g., intravenous infusion).

In some embodiments, the targeting agent can include a polypeptide (or targeting polypeptide) that binds to and/or complexes with the proteolytically cleaved extracellular fragment of the Ig superfamily cell adhesion molecule. The targeting polypeptide can include, consist essentially of, or consist of about 10 to about 50 amino acids and have an amino acid sequence that is substantially homologous to about 10 to about 50 consecutive amino acids of a homophilic binding portion or domain of the proteleolytically cleaved extracellular fragment of the Ig superfamily cell adhesion molecule. By substantially homologous, it is meant the targeting polypeptide has at least about 80%, about 90%, about 95%, about 96%, about 97%, about 98%, about 99% or about 100% sequence identity with a portion of the amino acid sequence of the binding portion of the proteleolytically cleaved extracellular fragment of the Ig superfamily cell adhesion molecule.

In one example, the homophilic binding portion of the Ig superfamily cell adhesion molecule can include, for example, the Ig domain of the cell adhesion molecule. In another example, where the Ig superfamily cell adhesion molecule is PTPμ, the homophilic binding portion can include the Ig binding domain and the MAM domain.

In another aspect, the targeting polypeptide can have an amino acid sequence that is substantially homologous to about 10 to about 50 consecutive amino acids of the Ig binding domain and/or MAM domain of PTPμ (e.g., SEQ ID NO: 1) and readily cross the blood brain barrier when systemically administered to a subject. The development of the PTPμ targeting peptides can be based on a large body of structural and functional data. The sites required for PTPμ-mediated homophilic adhesion have been well characterized. In addition, the crystal structure of PTPμ can provide information regarding which regions of each functional domain are likely to be exposed to the outside environment and therefore available for homophilic binding and thus detection by a peptide probe.

In some embodiments, as illustrated schematically in FIG. 1, the proteolytically cleaved extracellular fragment of PTPμ (e.g., SEQ ID NO: 1) can include an amino acid sequence of SEQ ID NO: 2, the Ig and MAM binding region can comprise the amino acid sequence of SEQ ID NO: 3, and the polypeptide can have an amino acid sequence that is substantially homologous to about 10 to about 50 consecutive amino acids of SEQ ID NO: 2 or SEQ ID NO: 3. Examples of polypeptides that can specifically bind SEQ ID NO: 2 or SEQ ID NO: 3 and have an amino acid sequence that is substantially homologous to about 10 to about 50 consecutive amino acids of SEQ ID NO: 2 or SEQ ID NO: 3 are polypeptides that comprising an amino acid sequence selected from the group consisting of SEQ ID NO: 4, SEQ ID NO: 5, SEQ ID NO: 6, and SEQ ID NO: 7. Polypeptides comprising SEQ ID NO: 4, 5, 6, or 7 can recognize or bind to the MAM, Ig domain, or the FNIII repeats.

In other embodiments, a polypeptide that binds to and/or complexes with the proteolytically cleaved extracellular fragment of the Ig superfamily CAM or its receptor that is expressed by a cancer cell or another cell in the cancer cell microenvironment can have an amino acid sequence of SEQ ID NO: 8. SEQ ID NO: 8 is substantially homologous to a portion of SEQ ID NO: 1 or SEQ ID NO: 2 and can specifically bind to SEQ ID NO: 2 or SEQ ID NO: 3.

The targeting polypeptides can be subject to various changes, substitutions, insertions, and deletions where such changes provide for certain advantages in its use. In this regard, targeting polypeptides that bind to and/or complex with a proteolytically cleaved extracellular portion of an Ig superfamily cell adhesion molecule can be substantially homologous with, rather than be identical to, the sequence of a recited polypeptide where one or more changes are made and it retains the ability to function as specifically binding to and/or complexing with the proteolytically cleaved extracellular portion of an Ig superfamily cell adhesion molecule.

The targeting polypeptides can be in any of a variety of forms of polypeptide derivatives, that include amides, conjugates with proteins, cyclized polypeptides, polymerized polypeptides, analogs, fragments, chemically modified polypeptides, and the like derivatives.

The term "analog" includes any polypeptide having an amino acid residue sequence substantially identical to a sequence specifically shown herein in which one or more residues have been conservatively substituted with a functionally similar residue and that specifically binds to and/or complexes with the proteolytically cleaved extracellular portion of an Ig superfamily CAM as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Additional residues may also be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 1, 2, 3, 4, 5, 6, 7, 8, 9, 10, 11, and 12. In some cases, a peptide linker comprises two or more of the following amino acids: glycine, serine, alanine, and threonine.

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and aryl-amines (e.g., triethylamine, diisopropylamine, methylamine, dimethylamine and the like) and optionally substituted ethanolamines (e.g., ethanolamine, diethanolamine and the like).

The targeting polypeptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

It will be appreciated that the targeting polypeptide can bind to and/or complex with homophilic binding domains of proteolytically cleaved extracellular fragments of other Ig superfamily cell adhesion molecules, besides PTPs. For example, a similar molecular detection strategy described herein can be used with any other Ig superfamily CAM having a homophilic binding cell surface protein whose ligand binding site is known. A large variety of cell surface proteins, including other phosphatases, are cleaved at the cell surface (Streuli M, Saito H (1992) Expression of the receptor-linked protein tyrosine phosphatase LAR: proteolytic cleavage and shedding of the CAM-like extracellular region. EMBO J. 11:897-907; Anders L, Ullrich A (2006) Furin-, ADAM 10-, and gamma-secretase-mediated cleavage of a receptor tyrosine phosphatase and regulation of beta-catenin's transcriptional activity. Mol Cell Biol 26:3917-3934; Haapasalo A, Kovacs D M (2007) Presenilin/gamma-secretase-mediated cleavage regulates association of leukocyte-common antigen-related (LAR) receptor tyrosine phosphatase with beta-catenin J Biol Chem 282:9063-9072; Chow J P, Noda M (2008) Plasmin-mediated processing of protein tyrosine phosphatase receptor type Z in the mouse brain. Neurosci Lett 442:208-212; Craig S E, Brady-Kalnay S M. Tumor-derived extracellular fragments of receptor protein tyrosine phosphatases (RPTPs) as cancer molecular diagnostic tools. Anticancer Agents Med. Chem. 2011 January; 11(1):133-40.

Review. PubMed PMID: 21235433; PubMed Central PMCID: PMC3337336; Craig S E, Brady-Kalnay S M. Cancer cells cut homophilic cell adhesion molecules and run. Cancer Res. 2011 Jan. 15; 71(2):303-9. Epub 2010 Nov. 17. PubMed PMID: 21084269; PubMed Central PMCID: PMC3343737; Phillips-Mason P J, Craig S E, Brady-Kalnay S M. Should I stay or should I go? Shedding of RPTPs in cancer cells switches signals from stabilizing cell-cell adhesion to driving cell migration. Cell Adh Migr. 2011 Jul. 1; 5(4):298-305. Epub 2011 Jul. 1. PubMed PMID: 21785275; PubMed Central PMCID: PMC3210297). These proteins represent additional targets for that can be readily used by the skilled artisan for forming therapeutic polypeptides that can be used to treat cancers (Barr A J, Ugochukwu E, Lee W H, King O N, Filippakopoulos P, Alfano I, Savitsky P, Burgess-Brown N A, Muller S, Knapp S (2009) Large-scale structural analysis of the classical human protein tyrosine phosphatome. Cell 136:352-363).

Furthermore, the targeting polypeptides can be used as a starting point to develop higher affinity small molecules, antibodies, and/or antibody fragments with similar ligand binding capabilities. The development and screening of small molecules from pharmacophores of the polypeptides using, for example, in silico screening, can be readily performed, and the binding affinity of such identified molecules can be readily screened against targeting polypeptides using assays described herein to select small molecule agents.

In other embodiments, the targeting agent that specifically binds to or complexes with a proteolytically cleaved extracellular fragment of an immunoglobulin (Ig) superfamily cell adhesion molecule that is expressed by a cancer cell or another cell in the cancer cell microenvironment can be an antibody, such as a monoclonal antibody, a polyclonal antibody, or a humanized antibody. The antibody can include Fc fragments, Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

In some embodiments the antibody or fragment thereof can specifically or selectively bind to either the full length protein or a proteolytically cleaved extracellular fragment of PTPµ having the amino acid sequence of SEQ ID NO: 2. In other embodiments, the antibody or fragment thereof can specifically bind to the Ig and MAM binding region having the amino acid sequence of SEQ ID NO: 3 of the proteolytically cleaved extracellular fragment of PTPµ. In still other embodiments, the antibody or fragment thereof can specifically bind to an amino acid sequence selected from the group consisting of SEQ ID NO: 4, SEQ ID NO: 5, SEQ ID NO: 6, SEQ ID NO: 7, and SEQ ID NO: 8.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate an antibody or fragment thereof specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702, 892, 5,750,373, 5,821,047 and 6,127,132, each of which is incorporated herein by reference in their entirety.

In still other embodiments, the targeting agent can include a polypeptide-Fc chimera that can specifically bind to the extracellular fragment. Advantageously, in addition to its inhibition of cell adhesion function, the polypeptide-Fc chimera can induce immune responses, such as complementdependent lysis and antibody-dependent cellular cytotoxicity, that target tumor cells thereby eliciting anti-tumor activities.

Chimeric proteins that can combine the Fc regions of IgG with one or more domains of another protein, such as various cytokines and soluble receptors, are known. These chimeric proteins can be fusions of human Fc regions and human domains of another protein. These chimeric proteins would then be a "humanized Fc chimera". See, for example, Capon et al., Nature, 337:525-531, 1989; Chamow et al., Trends Biotechnol., 14:52-60, 1996); U.S. Pat. Nos. 5,116,964 and 5,541,087. The chimeric protein can be a homodimeric protein linked through cysteine residues in the hinge region of IgG Fc, resulting in a molecule similar to an IgG molecule without the $C_{H1}$ domains and light chains. Due to the structural homology, such Fc fusion proteins exhibit in vivo pharmacokinetic profile comparable to that of human IgG with a similar isotype. This approach has been applied to several therapeutically important cytokines, such as IL-2 and IFN-α, and soluble receptors, such as TNF-Rc and IL-5-Rc (See, for example, U.S. Pat. Nos. 5,349,053, 6,224,867 and 7,250,493).

In some embodiments, the polypeptide-Fc chimera is a chimeric molecule that includes a human sequence encoded polypeptide fused to a human Fc fragment and is capable of binding to or complexing with a proteolytically cleaved extracellular fragment of an immunoglobulin (Ig) superfamily CAM or its receptor that is expressed by a cancer cell or another cell in the cancer cell microenvironment.

The polypeptide portion of the polypeptide-Fc chimera used for methods described herein may be a polypeptide having an amino acid sequence that is substantially homologous to about 10 to about 50 consecutive amino acids of the Ig binding domain and/or MAM domain of PTPμ (e.g., SEQ ID NO: 1) and readily cross the blood brain bather when systemically administered to a subject. In some embodiments, the polypeptide can have an amino acid sequence that is substantially homologous to about 10 to about 50 consecutive amino acids of SEQ ID NO: 2 or SEQ ID NO: 3. Examples of polypeptides that can specifically bind SEQ ID NO: 2 or SEQ ID NO: 3 and have an amino acid sequence that is substantially homologous to about 10 to about 50 consecutive amino acids of SEQ ID NO: 2 or SEQ ID NO: 3 are polypeptides having an amino acid sequence selected from the group consisting of SEQ ID NO: 4, SEQ ID NO: 5, SEQ ID NO: 6, and SEQ ID NO: 7. In other embodiments, the polypeptide portion of the polypeptide-Fc chimera used for methods described herein may be a polypeptide having an amino acid sequence of SEQ ID NO: 8.

The polypeptide portion of the polypeptide-Fc chimera, similar to the targeting polypeptides described above, can be subject to various changes, substitutions, insertions, and deletions where such changes provide for certain advantages in its use. In this regard, polypeptide portion correspond to or be substantially homologous with, rather than be identical to, the sequence of a recited polypeptide where one or more changes are made and it retains the ability to function as specifically binding to and/or complexing with the proteolytically cleaved extracellular portion of an Ig superfamily cell adhesion molecule.

The Fc portion of the polypeptide-Fc chimera is a domain that binds an activating Fc receptor, such as an activating Fc Ig domain and includes the hinge region that allows for dimerization. The Fc portion of the polypeptide-Fc chimera can be readily adapted to render it species-specific. For use in a murine system, e.g., cells derived from a mouse, the Fc fragment used to generate polypeptide-Fc can be that of a murine origin. In some embodiments, an Fc fragment of the murine IgG2a can be used.

For use in a human subject, e.g., for cancer treatment, the Fc fragment used to generate the polypeptide-Fc chimera is of a human origin. In some embodiments, the polypeptide-Fc chimera comprises an activating Fc Ig domain. Among the four human IgG isotypes, an activating Fc domain of $IgG_1$ can be used for the preparation of the polypeptide-Fc chimera. In certain embodiments, the Fc portion can have an amino acid sequence of SEQ ID NO: 9.

It is appreciated that different antibody isotypes have a varying degree of cytotoxic potential in vivo (See, for example, Nimmerjahn F. & Ravetch J V., 2006, Immunity, 24:19-28). For example, the murine IgG2a and IgG2b isotypes are more efficient in clearing infections, such as bacterial infections and viral infections and in killing tumor cells than their $IgG_1$ or $IgG_3$ counterparts. This is attributable at least in part to differential ratios of activating versus inhibitory FcRs present in vivo. Similarly, with respect to human IgG isotypes, $IgG_1$ and $IgG_3$ have a stronger interaction with FcRs than $IgG_2$ or $IgG_4$. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human immunoglobulin $G_1$ and increased antibody-dependent cellular cytotoxicity (Cartron G. et al., 2002, Blood, 99: 754-758).

Thus, as shall be clear to the skilled artisan, it is possible to optimize the interaction between the Fc portion of the polypeptide-Fc chimera to its corresponding Fc receptor by strategically selecting or modifying the Fc allele used for preparing the polypeptide-Fc chimera. Accordingly, a mutant or an allotype of an Fc fragment can be used here for the polypeptide-Fc chimera described herein. A number of useful mutations within an Fc domain have been described, which can affect the interaction of an Fc and its receptor, the effector function of the Fc, as well as the half-life of the Fc-containing molecule. These include specific amino acid substitutions and/or modifications to carbohydrate moieties in the Fc. For review, see, for example, Liu et al., 2008, Immunological Reviews, 222:9-27; Nimmerjahn & Ravetch, 2007, Curr. Opin. Immunol., 19(2): 239-45.

In other embodiments, the polypeptide-Fc chimera can be engineered with an enhanced complement activity. Generally, complement can be activated by at least three pathways, leading to the formation of the membrane attack complex (MAC) C5b-9, which forms pores in the plasma membranes of target cells and causes their lysis. Clq binding to the Fc domain is a critical step in this process. Among the human IgG subclasses, only IgG1 and IgG3 can initiate the complement cascade. In some embodiments, mutations are introduced to the Fc domain of the polypeptide-Fc chimera, so as to promote Clq recruitment and the Clq-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the polypeptide-Fc contains the mutation, Lys326Trp, Glu333Ser or both.

In addition, it should be noted that when chimeric or fusion proteins with artificial sequences and activities are used for diagnostic applications, in some circumstances, patients administered such a chimeric or fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2, which is incorporated by reference herein; Liu et al., 2008, Immunological Reviews, 222:9-27. Such modifications may be useful for an effective design of the polypeptide-Fc chimera described herein.

The polypeptide-Fc chimera used in the methods may include a linking moiety that connects the polypeptide portion with an Fc fragment. In some cases, a hinge region of Fc fusion protein molecules serves as a spacer between the Fc region and the fused polypeptide (e.g., soluble receptor), allowing these two parts of the molecule to function separately.

In some embodiments, the Fc portion and the polypeptide portion that comprise a chimeric molecule are linked via a linking molecule which is not a contiguous portion of either the polypeptide or Fc portions and which covalently joins an amino acid of the polypeptide to an amino acid of Fc. As used herein, a linking molecule that is "not a contiguous portion" means that the polypeptide portion and the Fc portion of the chimera are connected via an additional element that is not a part of the polypeptide or immunoglobulin that is contiguous in nature with either of the chimeric portions and functions as a linker.

In some embodiments, the linking molecule may be a peptide linker. Where the linker is a peptide linker, the polypeptide-Fc chimera may be produced as a single recombinant polypeptide using a conventional molecular biological/recombinant DNA method.

Alternatively, a linking molecule may be a non-peptide linker. As used herein, a non-peptide linker useful for the method described herein is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers useful for Fc fusion molecules, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

Molecular biological and biochemical techniques for preparing an Fc chimera are known. In some embodiments, the polypeptide-Fc chimera can be produced by conventional recombinatory DNA methods. In other embodiments, the polypeptide-Fc chimera can be produced as a single (e.g., contiguous) recombinant polypeptide. In still other embodiments, two or more portions of the polypeptide-Fc can be produced as separate fragments and are subsequently linked together to yield the polypeptide-Fc chimera. For example, the polypeptide portion of the polypeptide-Fc chimera and an Fc portion of the polypeptide-Fc chimera can each be produced as separate recombinant polypeptides then fused together by a chemical linking means to yield the polypeptide-Fc. This production methodology may be preferred particularly in situations where a non-peptide linking molecule is employed. Similarly, this production methodology may be also preferred if a chimeric polypeptide-Fc does not fold correctly (e.g., does not properly bind a ligand) when made as a single contiguous polypeptide.

For the production of recombinant polypeptides, a variety of host organisms may be used. Examples of hosts include, but are not limited to: bacteria, such as E. coli, yeast cells, insect cells, plant cells and mammalian cells. Choice of a host organism will depend on the particular application of the polypeptide-Fc chimera. The skilled artisan will understand how to take into consideration certain criteria in selecting a suitable host for producing the recombinant polypeptide. Factors affecting selection of a host include, for example, post-translational modifications, such as phosphorylation and glycosylation patterns, as well as technical factors, such as the general expected yield and the ease of purification. Host-specific post-translational modifications of the polypeptide-Fc chimera, which is to be used in vivo, should be carefully considered because certain post-translational modifications are known to be highly immunogenic (antigenic).

In other embodiments, the targeting agent can be directly or indirectly labeled with a detectable moiety. The role of a detectable moiety is to facilitate the detection step of a diagnostic method by allowing visualization of the complex formed by binding of the molecular probe to the proteolytically cleaved extracellular fragment of the Ig superfamily cell adhesion molecule. The detectable moiety can be selected such that it generates a signal, which can be measured and whose intensity is related (preferably proportional) to the amount of the molecular probe bound to the tissue being analyzed. Methods for labeling biological molecules, such as polypeptides and antibodies are well-known in the art.

Any of a wide variety of detectable moieties can be used with the targeting agents described herein. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some embodiments, the molecular probes described herein may be used in conjunction with non-invasive imaging (e.g., neuroimaging) techniques for in vivo imaging of the molecular probe, such as magnetic resonance spectroscopy (MRS) or imaging (MRI), or gamma imaging, such as positron emission tomography (PET) or single-photon emission computed tomography (SPECT). The term "in vivo imaging" refers to any method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given detectable moiety. For instance, the type of instrument used will guide the selection of the stable isotope. The half-life should be long enough so that it is still detectable at the time of maximum uptake by the target, but short enough so that the host does not sustain deleterious effects.

In one example, the detectable moiety the detectable moiety can include a radiolabel, that is coupled (e.g., attached or complexed) with the targeting agent using general organic chemistry techniques. The detectable moiety can also include radiolabels, such as $^{123}$I, $^{131}$I, $^{125}$I, $^{18}$F, $^{11}$C, $^{75}$Br, $^{76}$Br, $^{124}$I, $^{13}$N, $^{64}$Cu, $^{32}$P, $^{35}$S, for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The detectable moiety can also include $^{123}$I for SPECT. The $^{123}$I can be coupled to the targeting agent can by any of several techniques known to the art. See, e.g., Kulkarni, Int. J. Rad. Appl. & Inst. (Part B) 18: 647 (1991), the contents of which are hereby incorporated by reference. In addition, detectable moiety can include any radioactive iodine isotope, such as, but not limited to $^{131}$I, $^{125}$I, or $^{123}$I. The radioactive iodine isotopes can be coupled to the targeting agent by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art.

The detectable moiety can further include known metal radiolabels, such as Technetium-99m ($^{99m}$Tc), $^{153}$Gd, $^{111}$In, $^{67}$Ga, $^{201}$Tl, $^{68}$Ga, $^{82}$Rb, $^{64}$Cu, $^{90}$Y, $^{188}$Rh, T(tritium), $^{153}$Sm, $^{89}$Sr, and $^{211}$At. Modification of the targeting agent to introduce ligands that bind such metal ions can be effected without undue experimentation by one of ordinary skill in the radiolabeling art. The metal radiolabeled molecular probes can then be used to detect cancers, such as GBM in the subject. Preparing radiolabeled derivatives of Tc99m is well known in the art. See, for example, Zhuang et al., "Neutral and stereospecific Tc-99m complexes: [99 mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Fluorescent labeling agents or infrared agents include those known to the art, many of which are commonly commercially available, for example, fluorophores, such as ALEXA 350, PACIFIC BLUE, MARINA BLUE, ACRIDINE, EDANS, COUMARIN, BODIPY 493/503, CY2, BODIPY FL-X, DANSYL, ALEXA 488, FAM, OREGON GREEN, RHODAMINE GREEN-X, TET, ALEXA 430, CAL GOLD™, BODIPY R6G-X, JOE, ALEXA 532, VIC, HEX, CAL ORANGE™, ALEXA 555, BODIPY 564/570, BODIPY TMR-X, QUASAR™ 570, ALEXA 546, TAMRA, RHODAMINE RED-X, BODIPY 581/591, CY3.5, ROX, ALEXA 568, CAL RED, BODIPY TR-X, ALEXA 594, BODIPY 630/650-X, PULSAR 650, BODIPY 630/665-X, ALEXA 647, IR800, and QUASAR 670. Fluorescent labeling agents can include other known fluorophores, or proteins known to the art, for example, green fluorescent protein. The disclosed targeting agents can be coupled to the fluorescent labeling agents, administered to a subject or a sample, and the subject/sample examined by fluorescence spectroscopy or imaging to detect the labeled compound.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The disclosed targeting agents can be coupled to the quantum dots, administered to a subject or a sample, and the subject/sample examined by fluorescence spectroscopy or imaging to detect the labeled compound.

Numerous magnetic resonance imaging (MRI) contrast agents are known to the art, for example, positive contrast agents and negative contrast agents. The disclosed targeting agents can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iron oxide, or the like. Typical contrast agents include gadolinium(III)chelates, such as gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In some embodiments, the targeting agent can be coupled to the detectable moiety using a linking molecule. The linking molecule may be a peptide linker. Alternatively, a linking molecule may be a non-peptide linker.

The molecular probe described herein can be administered to the subject by, for example, systemic, topical, and/or parenteral methods of administration. These methods include, e.g., injection, infusion, deposition, implantation, or topical administration, or any other method of administration where access to the tissue by the molecular probe is desired. In one example, administration of the molecular probe can be by intravenous injection of the molecular probe in the subject. Single or multiple administrations of the probe can be given. "Administered", as used herein, means provision or delivery of a molecular probe in an amount(s) and for a period of time(s) effective to label cancer cells in the subject.

Molecular probes described herein can be administered to a subject in a detectable quantity of a pharmaceutical composition containing a molecular probe or a pharmaceutically acceptable water-soluble salt thereof, to a patient.

Formulation of the molecular probe to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the molecular probe to the cancer cells.

The molecular probes administered to a subject can be used in a method to detect and/or determine the presence, location, and/or distribution of cancer cells, i.e., cancer cells associated with proteolytically cleaved extracellular fragments of Ig superfamily cell adhesion molecules, in an organ or body area of a patient. The presence, location, and/or distribution of the molecular probe in the animal's tissue, e.g., brain tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., brain tissue. The distribution of the molecular probe may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the molecular probes may be administered to a subject to assess the distribution metastatic cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of brain on the tumor margin that are outside the tumor edge that appear to be grossly normal but are infiltrated by dispersing tumor cells upon histological examination.

Molecular probes that specifically bind to and/or complex with proteolytically cleaved Ig superfamily cell adhesion molecules (PTPµ) associated with metastatic cells can be used in intra-operative imaging techniques to guide surgical resection and eliminate the "educated guess" of the location of the tumor margin by the surgeon. Previous studies have determined that more extensive surgical resection improves patient survival Stummer W, Novotny A, Stepp H, Goetz C, Bise K, Reulen H J (2000) Fluorescence-guided resection of glioblastoma multiforme by using 5-aminolevulinic acid-induced porphyrins: a prospective study in 52 consecutive patients. J Neurosurg 93:1003-1013. Fluorescence-guided resection of glioblastoma multiforme by using 5-aminolevulinic acid-induced porphyrins: a prospective study in 52 consecutive patients. Stummer W, Novotny A, Stepp H, Goetz C, Bise K, Reulen H J (2000) Fluorescence-guided resection of glioblastoma multiforme by using 5-aminolevulinic acid-induced porphyrins: a prospective study in 52 consecutive patients. J Neurosurg 93:1003-1013. Thus, molecular probes that function as diagnostic molecular imaging agents have the potential to increase patient survival rates.

In some embodiments, to identify and facilitate removal of cancers cells, microscopic intra-operative imaging (IOI) techniques can be combined with systemically administered or locally administered molecular probes described herein. The molecular probe upon administration to the subject can target and detect and/or determine the presence, location, and/or distribution of cancer cells, i.e., cancer cells associated with proteolytically cleaved extracellular fragments of Ig superfamily cell adhesion molecules, in an organ or body area of a patient. In one example, the molecular probe can be combined with IOI to identify malignant cells that have infiltrated and/or are beginning to infiltrate at a tumor brain margin. The method can be performed in real-time during brain or other surgery. The method can include local or systemic application of the molecular probe that includes a detectable moiety, fluorescent or MRI contrast moiety. An imaging modality can then be used to detect and subsequently gather image data. The resultant image data may be used to determine, at least in part, a surgical and/or radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

Another embodiment described herein relates to a method of monitoring the efficacy of a cancer therapeutic or cancer therapy administered to a subject. The methods and molecular probes described herein can be used to monitor and/or compare the invasion, migration, dispersal, and metastases of a cancer in a subject prior to administration of a cancer therapeutic or cancer therapy, during administration, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect, a method of monitoring the efficacy of a cancer therapeutic is provided. More specifically, embodiments of the application provide for a method of monitoring the efficacy of a cancer therapy.

The method of monitoring the efficacy of a cancer therapeutic can include the steps of administering in vivo to the animal a molecular probe as described herein, then visualizing a distribution of the molecular probe in the animal (e.g., with an in vivo imaging modality as described herein), and then correlating the distribution of the molecular probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a molecular probe pre and post cancer therapy.

In some embodiments, the molecular probe bound to and/or complexed with the proteolytically cleaved extracellular fragment of the Ig superfamily cell adhesion molecule is detected in the subject to detect and/or provide the location and/or distribution of the cancer cells in the subject. The location and/or distribution of the cancer cells in the subject can then be compared to a control to determine the efficacy of the cancer therapeutic and/or cancer therapy. The control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the molecular probe to the subject and detecting the molecular probe bound to and/or complexed with cancer cells in the subject prior to administration of the cancer therapeutic and/or cancer therapy.

In certain embodiments, the methods and molecular probes described herein can be used to measure the efficacy of a therapeutic administered to a subject for treating a metastatic, invasive, or dispersed cancer. In this embodiment, the molecular probe can be administered to the subject prior to, during, or post administration of the therapeutic regimen and the distribution of cancer cells can be imaged to determine the efficacy of the therapeutic regimen. In one example, the therapeutic regimen can include a surgical resection of the metastatic cancer and the molecular probe can be used to define the distribution of the metastatic cancer pre-operative and post-operative to determine the efficacy of the surgical resection. Optionally, the methods and molecular probes can be used in an intra-operative surgical procedure, such as a surgical tumor resection, to more readily define and/or image the cancer cell mass or volume during the surgery.

In other embodiments, the molecular probes can be conjugated to a therapeutic agent and administered to a subject for treating a cancer, such as a metastatic cancer. In this embodiment, the molecular probe can be administered to the subject prior to, during, or post administration of the therapeutic agent and the distribution of metastatic cells can be targeted with the therapeutic agent.

The therapeutic agent can include an anti-proliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In some embodiments, the targeting agent can be coupled to the therapeutic agent using a linking molecule. The linking molecule may be a peptide linker. Alternatively, a linking molecule may be a non-peptide linker.

The following examples are included to demonstrate preferred embodiments.

Example 1

In this Example, we evaluated the ability of the fluorescent PTPµ probe to label the adjacent microenvironment of dispersed cell populations of CNS-1-GFP and LN-229-GFP intracranial tumors as assayed using the 3-D cryo-imaging system. Live mice bearing brain tumors were injected intravenously with the Cy5 PTPµ probe. Brains were imaged post-mortem using whole-brain macroscopic fluorescence imaging and the cryo-imaging system. Fluorescent signals were analyzed to determine the co-localization of the Cy5 labeled PTPµ probe with the GFP labeled dispersed tumor cells in the entire mouse brain. The 3-D cryo-images shown offer exquisite detail of glioma tumor cell dispersal and molecular detection by the PTPµ probe. Our results indicate that the PTPµ probe detected 99% of tumor cells at the main tumor site and in dispersed cells up to 3.5 mm from the main tumor. Therefore, the PTPµ imaging probe has potential translational significance for molecular imaging of tumors, guiding a more complete resection of tumors and to serve as a molecular targeting agent to deliver chemotherapeutics to the main tumor mass and distant dispersive tumor cells.

Materials and Methods

Peptide Synthesis and Conjugation

The SBK2 peptide (GEGDDFNWEQVNTLTKPTSD) (SEQ ID NO: 5) and a scrambled sequence of the SBK2 peptide (GFTQPETGTDNDLWSVDNEK) (SEQ ID NO: 10) were synthesized using a standard Fmoc based solid phase strategy with an additional N-terminal glycine residue as previously described. Following synthesis, the N-terminal glycine residues of the SBK2 and scrambled probes were conjugated to Cy5 NHS ester dye (GE Healthcare Life Sciences, USA).

Orthotopic Xenograft Intracranial Tumors

CNS-1 (from Mariano S. Viapiano or LN-229 (American Type Culture Collection, Manassas, Va.) cell lines were infected with GFP encoding lentivirus and used for intracranial implantation in 4-6 week old NIH athymic nude male mice (NCr-nu/+, NCr-nu/nu, 20-25 g each) as previously described. GFP fluorescence in 100% of cells was verified prior to use in intracranial implants. The CNS-1 cell line was authenticated by Research Animal Diagnostic Laboratory at the University of Missouri (Columbia, Mo.) for interspecies and mycoplasma contamination by PCR analysis. $5 \times 10^4$ (LN-229) or $2 \times 10^5$ (CNS-1) cells were implanted per mouse.

In Vivo Labeling of Intracranial Tumors

Imaging experiments were performed at 10-11 days for CNS-1 and 4-8 weeks for LN-229, to allow for optimal tumor growth and cell dispersal in these two cell lines. Live mice were injected via lateral tail vein with either SBK2-Cy5 or scrambled-Cy5 probes diluted to 15 µM in PBS (3 nMol total probe delivered). Following a 90-min interval for clearance of unbound probe, the animals were sacrificed and the brains removed for whole-brain imaging using the MAESTRO FLEX In-Vivo Imaging System (Cambridge Research & Instrumentation, Inc. (CRi), Woburn, Mass.) Immediately after imaging, the brains were embedded in Tissue-Tek OCT compound (Sakura Finetek U.S.A., Inc. Torrance, Calif.), frozen in a dry ice/ethanol slurry and cryo-imaged. Of note, delivery of multiple doses of either the SBK2-Cy5 or scrambled-Cy5 probes did not result in deleterious effects on mouse health (data not shown).

Cryo-imaging of Tissue Samples

Frozen brains were alternately sectioned and imaged using the previously described Case Cryo-Imaging System at a section thickness of 15 µm and a resolution of 11×11×15 µm. Brightfield and fluorescence images were acquired for each of the brains using a low light digital camera (Retiga Exi, QImaging Inc., Canada), an epi-illumination fluorescent light source (Lumen200 PRO, Prior Scientific' Rockland, Mass.) and fluorescence filters for GFP (Exciter: HQ470/40x, Dichroic: Q495LP, Emitter: HQ500LP) or Cy5 (Exciter: FF01-628/40-25, Dichroic: FF660-Di01-25×36, Emitter: FF01-692/40-25; Semrock, Rochester, N.Y.). Single GFP expressing cells were readily detected with this system. Brightfield and fluorescence exposure settings were identical for SBK2-Cy5 and scrambled-Cy5 probe treated brains. Eight brains implanted with CNS-1-GFP cells and six brains with LN-229-GFP cells were analyzed.

Image Processing Algorithms for Visualization of Tumor Cells and Vasculature

Methodologies for segmentation and visualization of the main tumor mass, dispersing cells, and vasculature have been described. Briefly, the main tumor mass was segmented using a fast 3-D region growth algorithm with intensity and gradient-based inclusion/exclusion criteria. Individual slice images were manually edited if necessary. Dispersed cells and clusters were detected by thresholding a Gaussian high pass filter image, discounting the masked main tumor mass. Autofluorecence of normal tissue is not a concern for false positive signals in both red and green channels as it is only less than 1% of the signal found in the vicinity of the main tumor and dispersed cells. Light scattering in tissue might appear as a false positive signal in Cy5 volumes, However, we processed Cy5 volumes with a next-image processing algorithm, and used attenuation and scattering parameters for brain tissue that were previously described. Similar parameters were applied for both SBK2-Cy5 and scrambled-Cy5 volumes. To find co-labeled cells/clusters we applied a logical AND operator between the dispersed cell and Cy5 volumes. The lower limit for the blood vessel detection algorithm was ~30 µm diameter. 3-D volumes of tumor, dispersed cells, Cy5 labeled cells, and vasculature were rendered using Amira software (Visage Imaging Inc., San Diego, Calif.), with modifications developed expressly for cryo-image data. Pseudocolors were chosen to give the best contrast between the different data volumes. Colors were green (main tumor), yellow (dispersing cells), pink (PTPµ probe labeled dispersed cells), and red (vasculature).

Quantitation of Cy5 Fluorescence

Cy5 fluorescence intensity of tumors and dispersed cells was quantified by Matlab software using next-image processed volumes for CNS-1 and LN-229 tumors labeled with SBK2-Cy5 or scrambled-Cy5 probes, which normalized the signal to background fluorescence. Total fluorescence signal was then normalized for tumor volume. SBK2-Cy5 analysis: N=5 tumors for both CNS-1 and LN-229. Scrambled-Cy5 analysis: N=3 tumors for CNS-1 and one tumor for LN-229.

Distance Analysis of SBK2-Cy5 Probe Labeled Dispersed Cells

The distance between the main tumor mass and dispersed cells was determined using a 3-D morphological distance algorithm. Briefly, the algorithm detects the presence of fluorescent voxels in a series of 3-D dilations from the tumor edge outward. Voxel size was 11×11×15 µm, approximately the size of single cells. Dilations within 500 µm of the tumor edge were discarded to reduce nonspecific errors and to focus on the population of cells that had dispersed the greatest distance from the main tumor mass. Comparisons were made between the average dispersed cell population and the average SBK2-Cy5 labeled dispersed cell population for each 500 µm distance increment from a total of four brains.

Statistical Analysis

Results from the morphological distance algorithm described above were segmented into incremental distances of 500 µm from the tumor edge, and averaged from four brains. The standard deviation was calculated in Excel from the range of all values within each plotted distance increment for the four brains. The standard error was calculated in Excel using the standard deviation for each data point shown.

Results

Figure 4:
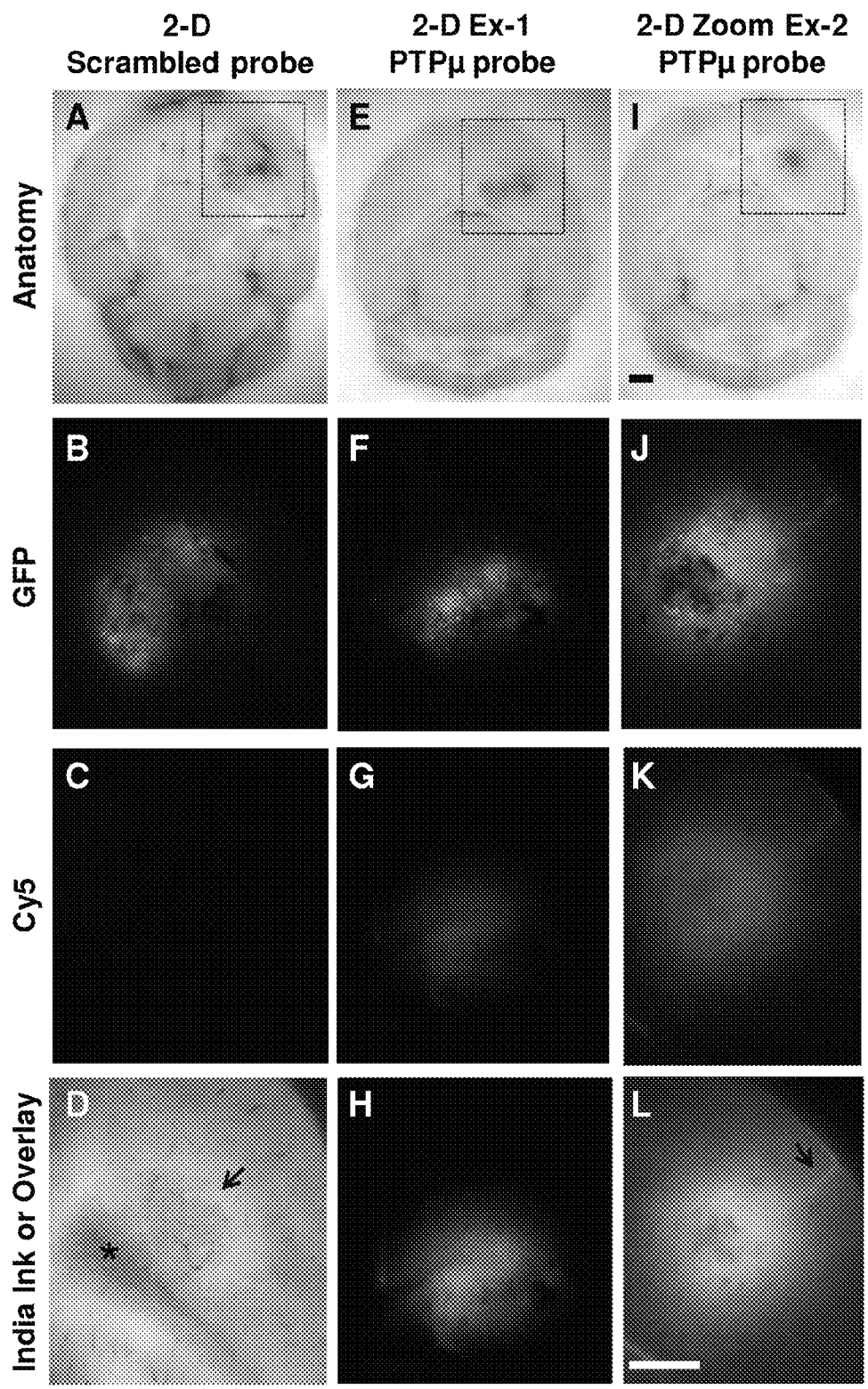
FIGS. 4(A-L) illustrate images showing CNS-1 glioma tumors and dispersing cells labeled by the PTPµ probe. Unfixed mouse brains containing xenografts of GFP-expressing CNS-1 cells were cryo-imaged following in vivo labeling with scrambled probe (A-C) or PTPµ probe (E-L). Two-dimensional block face images are shown for brightfield (A, E, I), with boxed regions that correspond to the views shown for GFP fluorescence (tumor; B, F, J) and Cy5 fluorescence (PTPµ probe; C, G, K) in each column. An overlay of GFP and Cy5 fluorescence demonstrates extensive labeling of the dispersed glioma cells with the PTPµ probe (H, L). In tumors with minimal cell dispersal (F), labeling with the PTPµ probe is localized to the main tumor (G, H). PTPµ probe labels diffusely dispersing cells in a tightly focused pattern when cells migrate as a stream along a defined structure, such as a blood vessel (K, L—see arrow). Brightfield image of a tumor from a brain that was perfused with India Ink (D) to illustrate leakiness of the vasculature. Scale bar in (I) represents 1 mm for panels (A, E, I) and the scale bar in (L) represents 1 mm for panels (B-D, F-H, J-L).

A PTPµ targeted probe was developed for the molecular recognition of glioma cells. Intracranial tumors of glioma cells expressing GFP were labeled with the PTPµ targeted probe (SBK2-Cy5) or with a scrambled version of the PTPµ probe (scrambled-Cy5) through intravenous administration. The main tumors were brightly labeled with the SBK2-Cy5 probe in all cases examined, whereas the scrambled probe resulted in no significant signal above background within the tumor (FIG. 4). Ten day CNS-1-GFP intracranial tumors were labeled in vivo with the PTPµ probe by intravenous injection for 90 minutes prior to sacrifice and post-mortem imaging. This time frame for probe clearance was determined empirically to provide optimal signal to noise (background) ratio of Cy5 fluorescence. The results from the two-dimensional block face images demonstrate bright PTPµ probe fluorescence (FIG. 4 G,K) within the main GFP-positive tumor (FIG. 4 F,J) in all cases. Cy5 fluorescence signal from PTPµ probe labeling also closely corresponded with the pattern of cell dispersal away from the main tumor (FIG. 4 H,L). In contrast, the scrambled probe did not appreciably label GFP-positive tumor cells above background (FIG. 4 A-C). Quantitation of Cy5 fluorescence intensity from the CNS-1 main tumors and dispersed cell populations labeled with the PTPµ probe was 73.5+/−16.2 (n=5 brains), compared with 7.2+/−2.3 (n=3 brains) for the scrambled probe.

The blood-brain bather is thought to be leaky within the main tumor in humans, a feature that is required for agents such as gadolinium to contrast brain tumors against the normal brain background. We examined the blood brain barrier integrity in our mouse model system by perfusing with dilute India Ink prior to removal of the brain containing a tumor. Vasculature of the perfused brain was contrasted black against the brain parenchyma, and blood vessels that coursed through the tumor were clearly defined, but there was no major accumulation of India Ink within the main tumor (arrowhead in FIG. 4d). Based on this result, we speculate that regions within the tumor and distant from the tumor edge likely have an intact blood-brain bather, suggesting that the PTPµ probe may be able to cross the blood-brain barrier to detect dispersing tumor cells.

Figure 5:
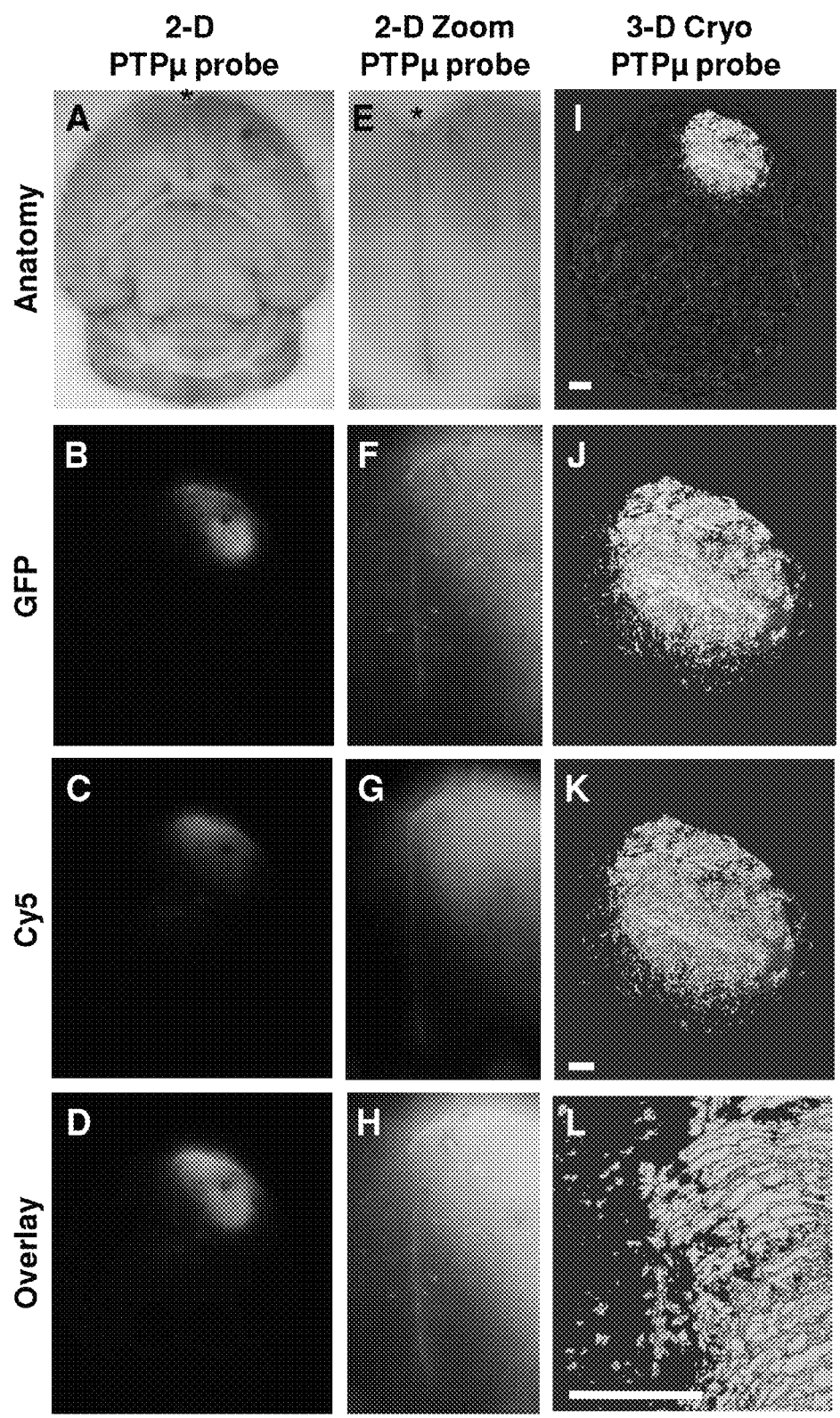
FIGS. 5(A-L) illustrate images showing the PTPµ probe specifically labels CNS-1 glioma cells that have dispersed from the main tumor. Unfixed mouse brains containing xenografts of GFP-expressing CNS-1 cells were cryo-imaged following in vivo labeling with PTPµ probe (A-H). Two-dimensional block face images are shown for brightfield (A, E), GFP fluorescence (tumor; B, F) and Cy5 fluorescence (PTPµ probe; C, G). An overlay of GFP and Cy5 fluorescence demonstrates extensive labeling of the dispersed glioma cells with the PTPµ probe (D, H). A high magnification image demonstrates that the PTPµ probe labels a stream of dispersing tumor cells (F) at the midline (asterisk) (G, H). Three-dimensional reconstruction of the tumor labeled with PTPµ probe is illustrated as main tumor (green), and dispersing cells (yellow) in a magnified view (J). Complete vasculature for this brain specimen is also shown (I). Dispersed cells co-labeled with PTPµ probe are pseudo-colored pink (K). (L) A magnified view of the tumor shown in (K) illustrates co-labeled cells along the midline, which correspond with the labeled midline cells in the 2-D overlay image (H). Scale bar in (I) represents 1 mm for panels (A-D,I). Scale bar in (K) represents 500 µm for panels (J-K). Scale bar in (L) represents 500 µm for panels (E-H,L).

The brains were then subjected to cryo-imaging analysis (FIG. 5). The cryo-imaging system obtained 2-D, microscopic bright-field anatomical images, including vasculature, and multi-spectral fluorescence images of tumor and probe. We refined our previous method to segment and visualize the vasculature, main tumor mass, and dispersing cells to highlight the PTPµ probe labeling of only the dispersive glioma cells and cell clusters (refer to Materials and Methods section). 3-D volumes were created for the main tumor mass (pseudo-colored green) and vasculature (pseudo-colored red). Glioma cells no longer physically connected in any dimension to the main tumor were pseudo-colored yellow to indicate tumor cell dispersal. To specifically visualize the PTPµ probe overlay in 3-D, the population of dispersing cells that was co-labeled with the PTPµ probe (Cy5 fluorescence) was pseudo-colored pink by the computer program.

The rat CNS-1 glioma cell line rapidly disperses to distances of several millimeters from the main tumor. A gradient of PTPµ probe fluorescence (FIG. 5 C,G) was observed that encompasses the wave of GFP-positive cell dispersal from the tumor (FIG. 4 B,F,J). Streams of CNS-1-GFP cells migrating along a defined structure were highlighted against the background tissue by the PTPµ probe (FIG. 4 G,H,K,L).

Figure 6:
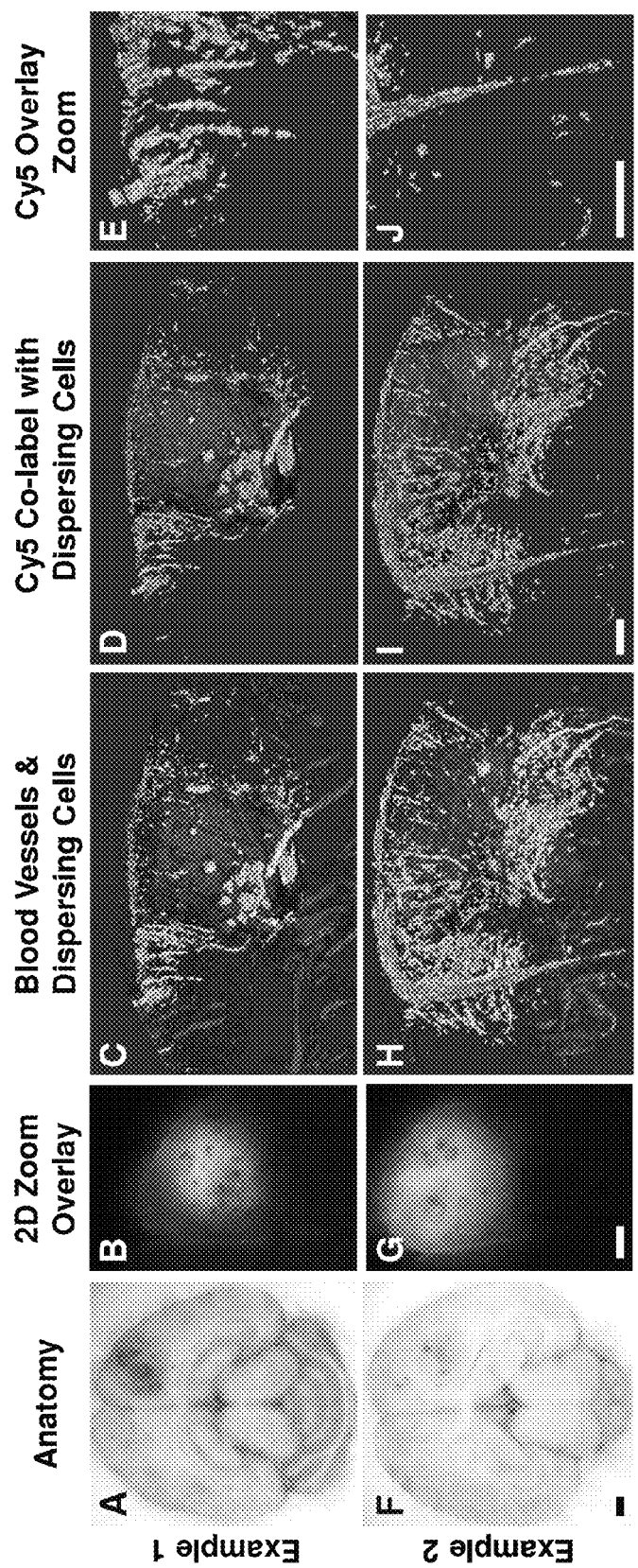
FIGS. 6(A-J) illustrate three-dimensional views of dispersed cells from CNS-1 intracranial tumors labeled by the PTPµ probe. Unfixed mouse brains containing xenografts of GFP-expressing CNS-1 cells were cryo-imaged and reconstructed in 3 dimensions following in vivo labeling with the PTPµ probe. Two-dimensional block face images are shown for brightfield (A, F), and 2-D block face zoomed overlay of GFP (tumor) and Cy5 fluorescence (PTPµ probe; B, G) for two brain tumors. Three-dimensional reconstructions of the same tumor specimens showing the main tumor mass (pseudo-colored green), dispersed tumor cells (pseudo-colored yellow), and vasculature (pseudo-colored red) illustrate that the dispersing cells often migrate on blood vessels (C, H). The total dispersing cell population is extensively co-labeled with the PTPµ probe (D, I), as shown pseudo-colored pink. Magnified views from (D, I) illustrate that PTPµ co-labeled cells are detected several millimeters from the main tumor (E, J). Scale bar in F represents 1 mm for panels (A, F) and scale bar in G represents 1 mm for panels (B, G). Scale bar in I represents 500 µm for panels (C-D, H-I) and the scale bar in J represents 500 µm for panels (E, J).
Figure 7:
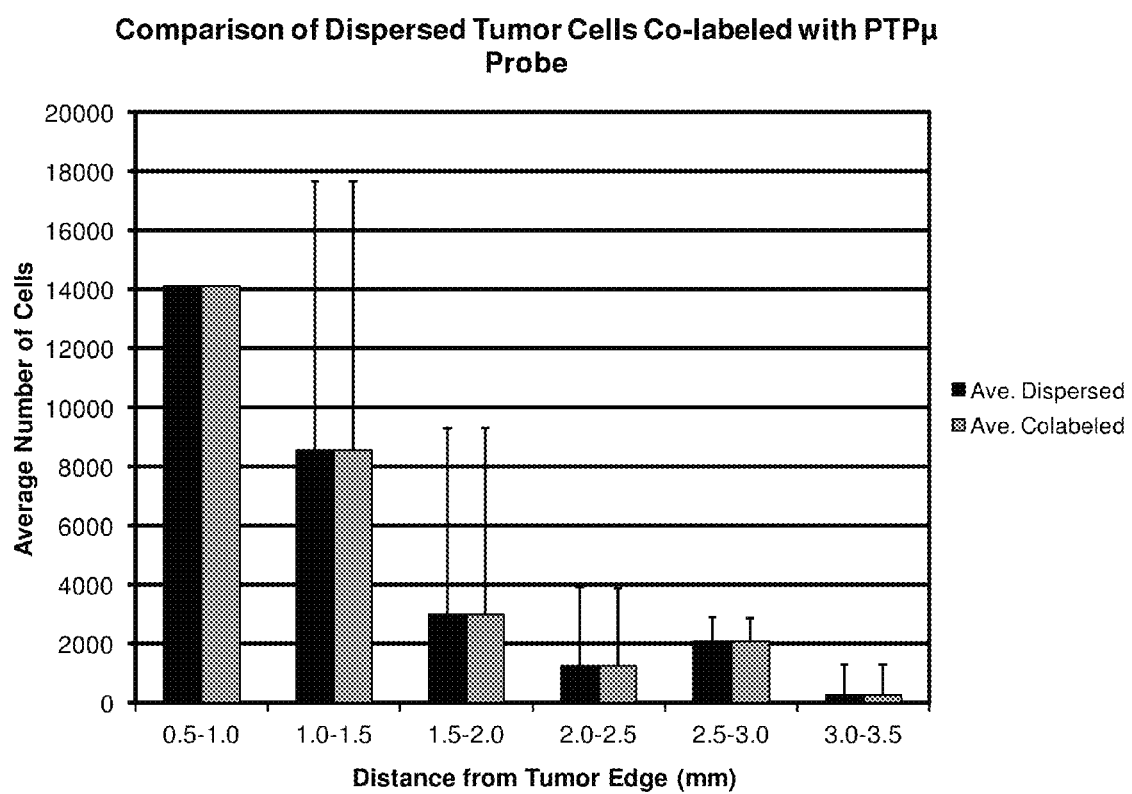
FIG. 7 illustrates a histogram showing the average number of GFP positive dispersing cells co-labeled with the PTPµ probe per unit distance from the main tumor, +/− standard error (n=4 tumors analyzed).

We have previously shown by immunoblot that the dispersive edge region of human glioblastoma tumors accumulates the PTPµ extracellular fragment, even though the tumor edge is comprised of normal brain cells and some dispersed tumor cells. In this study, the PTPµ probe fluorescent signal was often brighter in the region of lower GFP-fluorescence, which corresponds to the area of tumor cell dispersal, than it was in the main tumor, which has higher GFP fluorescence (FIGS. 5 B-D and F-H). This result suggests that the dispersed cells may have more cleaved PTPµ extracellular fragment deposited in their adjacent microenvironment than in the main tumor, as recognized by the PTPµ probe. This results in a signal amplification at the tumor edge as PTPµ fragment accumulates over time. A magnified version of that same brain at the midline region of the frontal pole (asterisk) shows GFP dispersing cells (FIG. 5F) are labeled with the PTPµ probe (Cy5: FIG. 5 G-H) in two-dimensional block face images. Three-dimensional reconstruction of the tumors illustrates a GFP-positive main tumor (pseudo-colored green) with a large population of GFP-labeled cells that disperse in many directions (pseudo-colored yellow) (FIGS. 5I and J). Analysis of the PTPµ probe labeling of only the GFP-positive dispersed cell population (pseudo-colored yellow) indicates that greater than 99% of the total dispersed cells were co-labeled with the PTPµ probe (pseudo-colored pink) (FIGS. 5K and L and FIG. 7). Evaluation of additional CNS-1-GFP intracranial tumors labeled with the PTPµ probe demonstrated that the probe was highly effective at labeling the dispersed cell population (FIG. 6). In the two examples shown, a substantial amount of cell dispersal is evident over the brain vasculature in many directions (FIGS. 6C and H).

Further analysis of the PTPµ probe-labeled CNS-1 intracranial tumors was performed to determine how far away from the main tumor mass dispersed cells could be labeled with the probe. Four CNS-1 intracranial tumors were analyzed to determine the total number of the dispersing cell population that was co-labeled with the PTPµ probe. The data was segmented into incremental distances of 500 µm from the tumor edge, and then averaged from the four brains. The results show that the PTPµ probe co-labels 99% of the dispersed cells to a maximum distance of 3.5 mm from the tumor edge (FIG. 7). In fact, the PTPµ probe is able to label even the distant dispersed tumor cells in multiple directions many millimeters from the main tumor mass (FIG. 6 D,E,I, J as well as FIG. 7).

Figure 8:
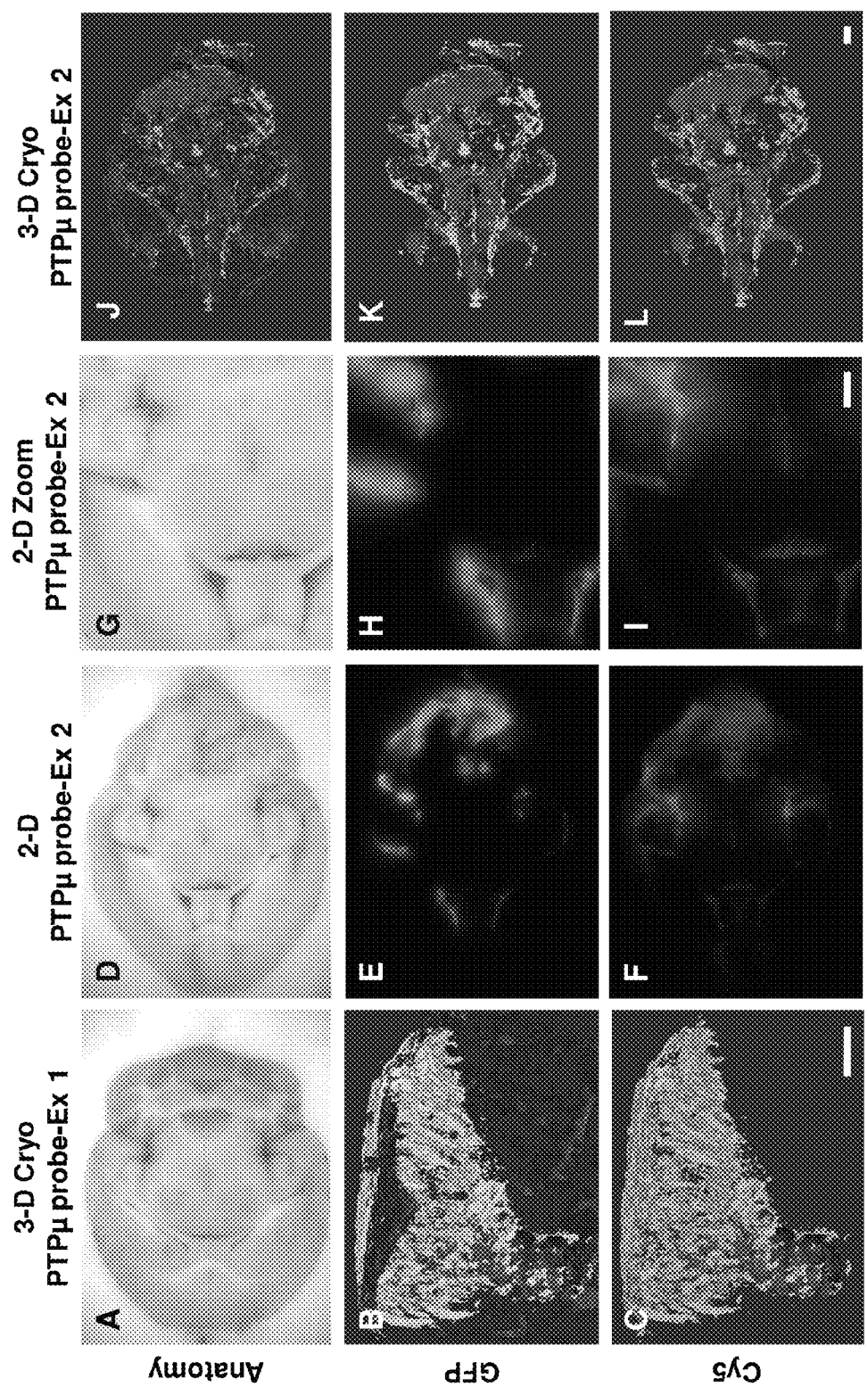
FIGS. 8(A-L) illustrate images showing dispersing cells from LN-229 intracranial tumors specifically labeled by the PTPµ probe. Unfixed mouse brains containing xenografts of GFP-expressing LN-229 cells were cryo-imaged and reconstructed in 3 dimensions following in vivo labeling with the PTPµ probe. Three-dimensional reconstruction of an LN229 tumor (A) shows the main tumor mass (pseudo-colored green), dispersed tumor cells (pseudo-colored yellow) and vasculature (pseudo-colored red) (B). PTPµ probe co-labeling of dispersing cells (pseudo-colored pink) was observed at great distances from the main tumor (C). A second tumor example where the LN229 tumor cells spread through the ventricles of the brain is shown (D-L). Two-dimensional block face images are shown for brightfield (D, G), GFP fluorescence (tumor; E, H) and Cy5 fluorescence (PTPµ probe; F, I). Comparison of GFP (E) and Cy5 (F) fluorescence in zoomed images (H, I) demonstrates extensive overlap in signal in this specimen. Three-dimensional reconstruction of the same tumor specimen is shown (J-L). In addition to the main tumor, the total dispersing cell population is extensively co-labeled with the PTPµ probe as shown pseudo-colored pink (L). Scale bar in (L) represents 500 µm for panels (A, D-F, J-L). Scale bar in (C) represents 500 µm for panels (B,C). Scale bar in (I) represents 500 µm for panels (G-I).

LN-229-GFP intracranial tumors require a minimum of four weeks growth to exhibit appreciable tumor cell dispersal. Labeling of LN-229-GFP tumors with the PTPµ probe resulted in a bright Cy5 fluorescence signal within the main GFP-positive tumor, and labeling of greater than 99% of the dispersed cell population (FIG. 8A-C). Quantitation of Cy5 fluorescence from the LN-229 main tumors and dispersed cell populations labeled with the PTPµ probe was 114.7+/−25.9 (n=5 brains), compared with 5.8 (n=1 brain) for the scrambled probe. In rare instances, glioma cells were deposited in close proximity to the lateral ventricle, resulting in extensive spread of cells along the ventricular walls, leptomeningeal regions, within the brainstem and in brain parenchyma at the cerebral/cerebellar junction (3-D reconstruction shown in FIG. 8J-L). Fluorescent signal from the PTPµ probe co-localized with much of this dispersed cell population (FIG. 8D-L).

Results from these experiments suggest that the PTPµ probe crosses the blood-brain barrier to label not only the main tumor mass, but also the vast majority of the dispersed tumor cells at a range up to 3.5 millimeters away from the main tumor mass (FIG. 7). In contrast, the scrambled-Cy5 probe did not label tumors (FIG. 4A-C). The PTPµ probe preferentially labeled the PTPµ extracellular fragment deposited in the adjacent tumor microenvironment of the dispersed cells (FIGS. 4G and K). These results suggest that the PTPµ probe is a marker of the microenvironment of the main tumor, tumor edge and dispersing cells, and can utilized for tumor imaging, a more complete surgical resection or can a viable molecular targeting agent to deliver therapeutics.

Example 2

This Example shows that SBK2 probe can be used as a diagnostic imaging tool. In this Example, we conjugated SBK2 to a gadolinium chelate [SBK2-Tris-(Gd-DOTA)$_3$] to generate an MR-detectable SBK2 probe. We compared the ability of SBK2-Tris-(Gd-DOTA)$_3$ to function as a contrast agent compared to a current MRI macrocyclic gadolinium chelate (Gadoteridol, ProHance) alone or to a scrambled probe linked to gadolinium [scrambled Tris-(Gd-DOTA)$_3$]. When intravenously injected into mice bearing flank tumors of human glioma cells, SBK2-Tris-(Gd-DOTA)$_3$ labeled the tumors within 5 minutes with a high level of contrast persisting for 2 hours post-injection. The contrast enhancement of SBK2-Tris-(Gd-DOTA)$_3$ was significantly higher than that observed with ProHance alone. These results demonstrate that SBK2-Tris-(Gd-DOTA)$_3$ labeling of PTPµ extracellular fragment retained in the tumor microenvironment is a more specific MR molecular imaging probe than a nonspecific gadolinium chelate and may be a useful tool for diagnosis of the extent of tumor dispersal before surgery and co-registering GBM tumor borders during surgical resection.

Materials and Methods

All reagents were used without further purification unless otherwise stated. Benzotriazol-1-yl-oxytripyrrolidinophosphonium hexafluorophosphate, 1-hydroxybenzotriazole hydrate, 2-chlorotritylchloride resin, and all of the Fmoc-protected amino acids were purchased from Chem-Impex International, Inc (Wood Dale, Ill.). Anhydrous N,N-diisopropylethyl amine and N,N-dimethylformamide were purchased from Alfa Aesar (Ward Hill, Mass.). Trifluoroacetic acid was purchased from Oakwood Products, Inc (West Columbia, S.C.).

Synthesis and Characterization of SBK2-Tris-(Gd-DOTA)$_3$ and Scrambled Tris-(Gd-DOTA)$_3$ The SBK2 peptide was conjugated to Gd-DOTA using an increased molar ratio of Gd-DOTA monoamide to peptide to generate an MR-visible probe [SBK2-Tris-(Gd-DOTA)$_3$]. A scrambled version of the SBK2 peptide was used to generate a nontargeted control agent [scrambled Tris-(Gd-DOTA)$_3$]. Peptide SBK2 with an N-terminal cysteine (C-GEGDDFN-WEQVNTLTKPTSD) (SEQ ID NO: 5) was synthesized using standard solid-phase peptide synthesis. Matrix-assisted laser desorption/ionization time-of-flight (MALDI-TOF; Autoflex Speed, Bruker) mass spectra (m/z, M$^+$) were given as follows: 2355.52 (observed) and 2355.00 (calculated). Scrambled peptide (C-GFTQPETGTDNDLWSVDNEK)

(SEQ ID NO: 10) was synthesized by the same method [MALDI-TOF (m/z, M+): 2355.56 (observed); 2355.00 (calculated)]. SBK2 was conjugated to maleimido-Tris-propargyl, then subsequently to azido-(Gd-DOTA). The reaction was traced by MALDI-TOF until Gd-DOTA was fully attached [MALDI-TOF (m/z, M$^+$):4664.87 (observed); 4664.62 (calculated); Inductively coupled plasma optical emission spectroscopy (ICP-OES) analysis for Gd3+ content: 9.56% (observed); 10.1% (calculated)]. Scrambled Tris-(Gd-DOTA)$_3$ was synthesized by the same method with a yield of 68% [MALDI-TOF (m/z, M+):4664.75 (observed); 4664.62 (calculated); ICP (Gd$^{3+}$ content): 9.68% (observed); 10.1% (calculated)].

The gadolinium content was measured by ICP-OES (Agilent 730 Axial ICP-OES; Agilent Technologies, Wilmington, Del.). Relaxation times were measured at 60 MHz (1.5 T) using a Bruker Minispec Relaxometer at 37° C. T1 was measured with an inversion recovery pulse sequence. T2 was measured using a Carr-Purcell-Meiboom-Gill sequence with 500 echoes collected.

Cell Culture and Flank Tumor Implants

The human LN-229 glioma cell line was purchased from American Type Culture Collection (Manassas, Va.) and cultured in Dulbecco's modified Eagle's medium supplemented with 5% FBS. Cells were infected with lentivirus encoding green fluorescent protein (GFP), diluted in BD Matrigel Matrix (BD Biosciences, Franklin Lakes, N.J.), and injected into both flanks of female nude athymic mice (NCr-nu/+, NCr-nu/nu, 20-25 g each). Approximately $1.4 \times 10^6$ cells were implanted per flank. To correlate tumor position with GFP fluorescence, mice were imaged using the Maestro FLEX In Vivo Imaging System as previously described. Tumor area was approximately 0.5 cm$^2$, as measured from GFP fluorescence images acquired with the Maestro just before MRI.

Molecular Imaging of Tumors with MRI

The MRI study was performed using a Bruker Biospec 7-T MRI scanner (Bruker Corp, Billerica, Mass.) with a 72-mm diameter cylindrical radio frequency coil. Mice bearing LN-229 flank tumors were imaged at 2 to 5 weeks after tumor implant. Mice were anesthetized with a 2% isoflurane-oxygen mixture in an isoflurane induction chamber. Tail veins were catheterized with a 30-gauge needle connected to a 1.2-m-long small diameter Tygon tubing filled with heparinized saline. The animals were moved into a magnet and kept under inhalation anesthesia with 1.5% isoflurane-oxygen through a nose cone. A respiratory sensor connected to a monitoring system (SA Instruments, Stony Brook, N.Y.) was placed on the abdomen to monitor rate and depth of respiration. The body temperature was maintained at 37° C. by blowing hot air into the magnet through a feedback control system. A group of three mice was used for each agent per experiment. Sagittal section images were acquired with a localizing sequence to identify the tumor location, followed by a fat suppression three-dimensional (3D) FLASH sequence [repetition time (TR)=8.5 ms, echo time (TE)=2.6 ms, average=3, 30° flip angle, in-plane field of view (FOV) =10 cm, 25-mm slab thickness] and a two-dimensional (2D) T 1-weighted spin echo sequence (TR=500 ms, TE=8.1 ms, average=2, in-plane FOV=3 cm, 1.2-mm slice thickness) before injection. After pre-injection baseline MRI acquisition, ProHance, the targeted SBK2 agent, or the nontargeted scrambled control was injected at a dose of 0.03 or 0.1 mmol Gd/kg by flushing with 60 μl of heparinized saline. Images were then acquired using the same sequences at 13 different time points after the injection for up to 120 minutes.

Image Processing and Analysis

Image analysis was performed by using Bruker ParaVision 4.0 imaging software. Regions of interest were drawn over the whole tumor in the 2D imaging plane and average signal intensity was measured. Contrast-to-noise ratios (CNRs) in the tumor were calculated at each time point and averaged from different mice (n=3) using the following equation: CNR=(St−Sm)/($δ_n$), where St and Sm denote the signal in tumor and adjacent thigh muscle and δn is the SD of noise estimated from the background air. The P values were calculated using a two-tailed Student's t test, assuming statistical significance at P<0.05. Color-coded display of relative contrast intensity in tumor was processed by SPIN (signal processing in NMR) software (MRI Institute for Biomedical Research, Detroit, Mich.).

Biodistribution Study

Mice from the MRI study were sacrificed at 7 days post-injection. The organ and tissue samples, including the brain, heart, kidneys, liver, lungs, spleen, skin, muscle, femur, and tumor, were resected and weighed. The tissue samples were liquified with nitric acid and prepared for ICP-OES measurement as previously described. The average gadolinium content in each sample was measured by ICP-OES (n=3 per contrast agent). The Gd content was calculated as the percentage of injected dose per gram of organ/tissue (% ID/g).

Histologic Analysis of Tumor Tissue Sections

LN-229-GFP flank tumors were excised and fixed with 4% paraformaldehyde in PEM buffer (80 mM Pipes, 5 mM EGTA, 1 mM magnesium chloride, 3% sucrose), pH 7.4, at 72 hours post-MR molecular imaging to allow for clearance of contrast agents. Tumors were embedded in Tissue Freezing Medium (Electron Microscopy Sciences, Hatfield, Pa.) in a dry ice ethanol slurry and cryosectioned at 7-μm intervals.

For probe labeling, tissue sections were blocked with 2% goat serum in phosphate-buffered saline for 20 minutes at room temperature, then incubated with SBK2-Texas Red or scrambled Texas Red probes diluted to 1 μMin block buffer for 1 hour at room temperature in dark conditions. The sections were rinsed with phosphate-buffered saline, coverslipped with Citifluor Antifadent Mounting Medium (Electron Microscopy Sciences), and imaged immediately at ×20 magnification on a Leica DMI 6000 B inverted microscope (Leica Microsystems GmbH, Wetzlar, Germany) using a Retiga EXi camera (QImaging, Surrey, BC) and Metamorph software (MolecularDevices, Downington, Pa.). Images were acquired across the entire tissue using bright-field and fluorescence optics for fluorescein (GFP) and Texas Red (probe). The resultant images were tiled and flattened to form a single composite image using Metamorph software. A human specific Vimentin antibody (clone SP20; Thermo Fisher Scientific, Fremont, Calif.) was used to detect the implanted LN-229 tumor cells and imaged as above.

Results

Synthesis and Characterization of SBK2-Tris-(Gd-DOTA)$_3$ and Scrambled Tris-(Gd-DOTA)$_3$ The SBK2 peptide was conjugated to Gd-DOTA using an increased molar ratio of Gd-DOTA monoamide to peptide to generate an MR-visible probe [SBK2-Tris-(Gd-DOTA)$_3$] for effective targeted contrast enhancement (FIG. 9). The final product had good water solubility. A scrambled version of the SBK2 peptide was used to generate a nontargeted control agent [scrambled Tris-(Gd-DOTA)$_3$]. The final products were characterized by MALDI-TOF and ICP-OES and with a Bruker Minispec Relaxometer. Both targeted and control contrast agents had similar relaxivity.

MR Tumor Molecular Imaging with SBK2-Tris-(Gd-DOTA)$_3$

Figure 11:
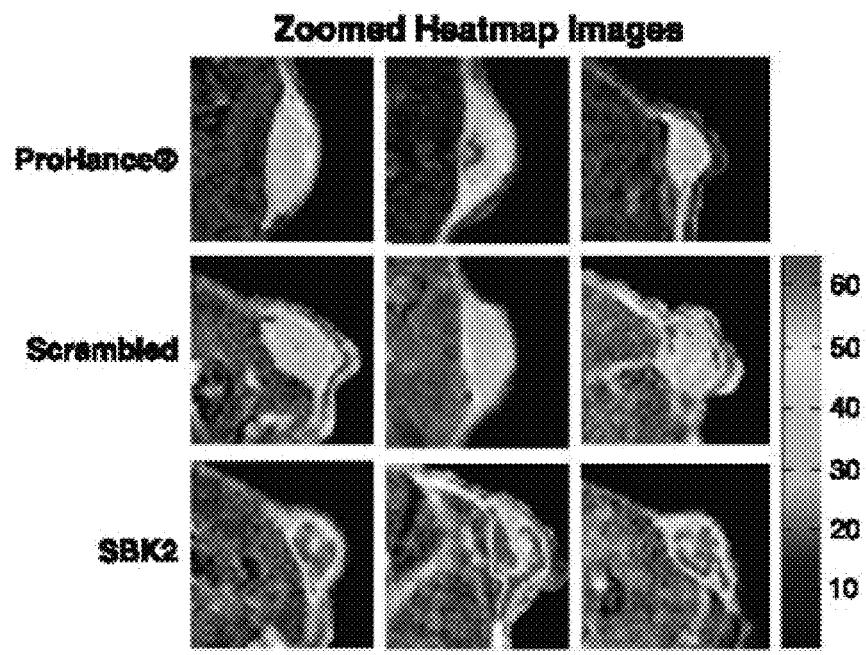
FIG. 11 illustrates digitally magnified axial 2D gradient images of tumors with heat map intensity overlays. Zoomed views of 5-minute T 1-weighted axial 2D gradient images of LN-229 flank tumor-bearing mice illustrate details of the heatmap intensity overlay in the tumors. Three representative examples are shown for the ProHance control, scrambled Tris-(Gd-DOTA)$_3$ (scrambled), and SBK2-Tris-(Gd-DOTA)$_3$ (SBK2) probes. Key indicates relative level of contrast intensity with red being the most intense.

Athymic (nu/nu) mice bearing LN-229 flank tumors (2-5 weeks post-implantation) were used for MRI studies. 2D axial T 1-weighted gradient echo images of mice were acquired before injection of contrast agents, then at 1-, 5-, 10-, 15-, 20-, 25-, and 30-minute intervals following intravenous injection of either ProHance, scrambled Tris-(Gd-DOTA)$_3$, or SBK2-Tris-(Gd-DOTA)$_3$ administered at a dose of 0.1 mmol/kg (FIG. 10). Representative examples of 2D axial images are shown in FIG. 10A for each contrast agent, with tumors indicated by white arrows. In comparison with the nontargeted contrast agents, the targeted SBK2-Tris-(Gd-DOTA)$_3$ agent resulted in greater enhancement of tumors that was maintained for a longer period of time (FIG. 10A). This improved tumor enhancement is better illustrated with heat map intensity overlays applied to the tumor regions (FIG. 10B). The color key indicates the relative enhancement level from lowest (purple) to highest (red). The tumor enhancement generated by the SBK2-Tris-(Gd-DOTA)$_3$ was greater than that observed for the scrambled or ProHance agents (FIG. 10B). Digitally magnified MRI and heat map intensity images show greater detail of the tumor enhancement achieved with each contrast agent for three separate tumors per agent (FIG. 11). The entire tumor was enhanced over adjacent tissues with all of the contrast agents evaluated. ProHance and scrambled Tris-(Gd-DOTA)$_3$ resulted in enhanced contrast of the tumor edge compared with the tumor center. This heterogeneous pattern is not due to necrosis because the LN-229 tumors grow slowly and do not exhibit necrosis in the time frame examined here. In comparison, the SBK2-Tris-(Gd-DOTA)$_3$ resulted in the most intense tumor enhancement, particularly in the tumor center. These results show that active targeting of the tumor with SBK2-Tris-(Gd-DOTA)$_3$ achieved greater penetration and contrast of the entire tumor.

Figure 12:
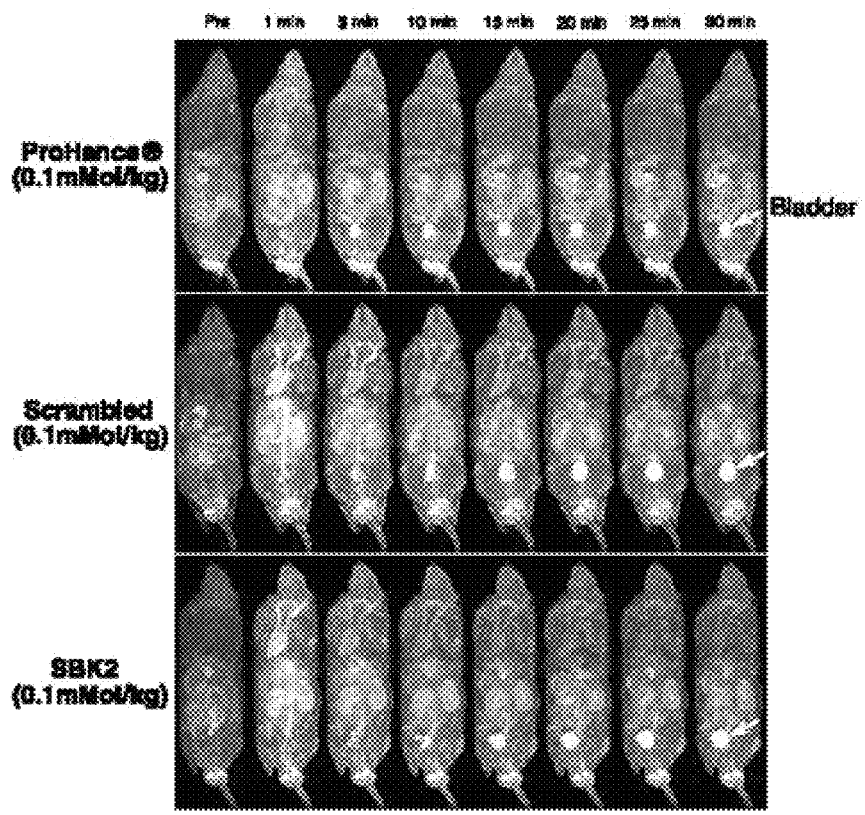
FIG. 12 illustrates representative T 1-weighted longitudinal 3D maximum intensity projection images of mice bearing LN-229 flank tumors before (Pre) and at 1, 5, 10, 15, 20, 25, and 30 minutes after intravenous injection of ProHance, scrambled Tris-(Gd-DOTA)$_3$, or SBK2-Tris-(Gd-DOTA)$_3$ contrast agents at 0.1 mmol Gd/kg in nude mice [n=4 for ProHance; n=6 for both scrambled Tris-(Gd-DOTA)$_3$ and SBK2-Tris-(Gd-DOTA)$_3$]. Arrow indicates bladder localization.

To examine the biodistribution of each contrast agent, 3D longitudinal T 1-weighted gradient echo images were also acquired for each mouse (FIG. 12). Contrast enhancement was observed in kidneys and other major organs at the earliest time points but was significantly decreased at later time points. Alternatively, enhancement of the urinary bladder (white arrows in FIG. 12) increased over time with all labeling agents, suggesting that the unbound agents were being cleared through renal filtration.

Quantitative Tumor Signal Analysis

Comparison of tumor enhancement was done using quantitative signal analysis. Regions of interest were drawn over the tumor and adjacent muscle tissue for each mouse, and the CNR was determined at each time point following injection of contrast agents. Dose-response tumor signal analysis was performed for ProHance or SBK2-Tris-(Gd-DOTA)$_3$ administered at 0.03 mmol/kg or 0.1 mmol/kg (FIG. 12A). The results indicate that the tumor contrast achieved with SBK2-Tris-(Gd-DOTA)$_3$ at 0.1 mmol/kg was significantly greater over the entire 30-minute period than that achieved with ProHance at 0.1 mmol/kg (P<0.05). Similar results were observed when comparing SBK2-Tris-(Gd-DOTA)$_3$ administered at 0.03 mmol/kg with ProHance (0.03 mmol/kg) at 10 to 30 minutes post-injection (P<0.05). Of interest, the lowest dose of SBK2-Tris-(Gd-DOTA)$_3$ (0.03 mmol/kg) resulted in tumor contrast that was similar to the contrast achieved with the highest dose of ProHance (0.1 mmol/kg). These results suggest that the targeted SBK2-Tris-(Gd-DOTA)$_3$ is superior for tumor enhancement.

To evaluate the dynamics of tumor enhancement over a longer period of time, quantitative signal analysis was performed in tumors over a 2-hour period following injection of contrast agents (FIG. 13B). The targeted agent SBK2-Tris-(Gd-DOTA)$_3$ showed improved tumor CNR when compared with the nontargeted scrambled Tris-(Gd-DOTA)$_3$ or ProHance. SBK2-Tris-(Gd-DOTA)$_3$ resulted in an approximate 55% increase in tumor CNR over scrambled Tris-(Gd-DOTA)$_3$ or ProHance at 15 to 45 minutes post-injection (P<0.001). At 60 to 120 minutes post-injection, the ProHance cleared more rapidly than SBK2-Tris-(Gd-DOTA)$_3$ resulting in greater than 110% increase in SBK2-Tris-(Gd-DOTA)$_3$ tumor CNR compared with ProHance (P<0.001). The SBK2-Tris-(Gd-DOTA)$_3$ tumor CNR was approximately 53% greater than the scrambled Tris-(Gd-DOTA)$_3$ tumor CNR at 60 to 90 minutes (P<0.001). The larger size of the scrambled Tris-(Gd-DOTA)$_3$ probe in comparison with ProHance may be partially responsible for its slower clearance rate between 60 and 120 minutes.

Biodistribution in Tissues

Tissue clearance of the targeted probes is important to avoid the accumulation of toxic gadolinium ions. The biodistribution of gadolinium was examined in the brain, heart, kidneys, liver, lungs, spleen, skin, muscle, femur, and tumor at 7 days post-injection of the ProHance, scrambled Tris-(Gd-DOTA)$_3$, or SBK2-Tris-(Gd-DOTA)$_3$ (FIG. 14). The gadolinium retention of scrambled Tris-(Gd-DOTA)$_3$ and SBK2-Tris-(Gd-DOTA)$_3$ was similar in all tissues. Low residual accumulation of approximately 0.39%, 0.91%, and 0.14% of injected targeted SBK2-Tris-(Gd-DOTA)$_3$ per gram of tissue was detected in spleen, kidney, and liver, while less than 0.1% was detected in all other tissues, including tumor. Accumulation of gadolinium from ProHance was less than 0.1% for all tissues examined.

Histology/Tumor Binding Specificity

LN-229-GFP flank tumors used for MRI were excised, fixed, and cryosectioned for histologic analysis. Zoomed MR and corresponding heat map images for the tumor are shown (FIG. 15A). The heterogeneous signal enhancement in the heat map overlay suggests that the target of the SBK2-Tris-(Gd-DOTA)$_3$ probe was concentrated in the tumor center and at the outer edge of the tumor. The corresponding flank tumor sections were incubated with SBK2-Texas Red or scrambled Texas Red probes. SBK2-Texas Red labeled the entire tumor with greatest intensity in the tumor center (FIG. 15B). This pattern is similar to that observed in the MR images following labeling with the SBK2-Tris-(Gd-DOTA)$_3$ probe. In contrast, the scrambled Texas Red probe did not label the tumor (FIG. 15B). These data indicate that the SBK2 probe recognized the flank tumors both in vitro and in vivo. Anti-human vimentin antibody was used to label all the human cells in the mouse flank. There is co-registration of the GFP-positive and vimentin-positive cells (FIGS. 15, A and B), demonstrating that all GFP-positive cells in the tumor xenograft are of human origin. The LN-229 flank tumor is encapsulated by GFP-negative cells and matrix, as shown in the magnified bright-field images in FIG. 15C. The proteolyzed extracellular fragment of PTPµ is retained both in the main tumor and, to a lower extent, in the encapsulated region, as illustrated by labeling with the SBK2-Texas Red probe (FIG. 15C). Similar gradients of PTPµ extracellular fragment, as detected by the SBK2 probe, have been observed previously.

The SBK2 probe offers several advantages over other MR molecular imaging reagents used to target cell surface proteins, including a fast time course to achieve peak labeling and rapid clearance from tumor tissue. The time course of peak labeling with the SBK2 probe occurs within 15 minutes (FIG. 13), while the SBK2 probe levels decline rapidly in the tumor tissue, typically at 2 hours (FIG. 13) with clearance from most tissues of the body by 7 days (FIG. 14). Peak binding for other cell surface probes occurs within 1 to 4 hours post-injection, and in the case of integrin binding RGD liposomes and nanoparticles, the rate of clearance is much slower, beginning 24 to 48 hours after injection.

The SBK2 probe may also function better than antibodies linked to contrast agents that are currently in development as MR molecular imaging reagents. As a 4.7-kDa peptide-based probe, SBK2-Tris-(Gd-DOTA)$_3$ is much smaller than an antibody and, therefore, is expected to have superior tissue penetration. Because PTPµ is endogenously processed and continuously deposited in tumor tissue to give rise to the extracellular fragment product, no additional exogenous amplification is required to visualize the probe. An anti-epidermal growth factor receptor (EGFR) antibody developed to visualize GBM cells requires an exogenous amplification step to provide sufficient contrast enhancement in vivo. This added step necessitates that the anti-EGFR antibody be injected 5 hours before the injection of the contrast agent, making it less suitable than the SBK2 probe for use in a clinical setting.

To conclude, the SBK2-Tris-(Gd-DOTA)$_3$ probe is a rapid and specific marker of glioma cells using MRI. This Example has established that the targeted SBK2-Tris-(Gd-DOTA)$_3$ probe is effectively delivered to LN-229 tumors for enhanced contrast and can be quickly cleared from the animal. A fluorescent SBK2 probe can cross the blood-brain barrier, even in areas of the brain where it is largely intact, to label most dispersive cells in GBM tumors. MRI can achieve the high resolution required to detect chains of dispersive GBM cells.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of detecting cancer cells and/or cancer cell metastasis, migration, dispersal, and/or invasion, the method comprising:
administering to a subject an amount of a molecular probe, the molecular probe comprising a targeting agent and a detectable moiety, the targeting agent specifically binding to and/or complexing with a proteolytically cleaved extracellular fragment of an immunoglobulin (Ig) superfamily cell adhesion molecule that is expressed by a cancer cell or another cell in the cancer cell microenvironment; and
detecting molecular probes bound to and/or complexed with the cancer cells to determine the location and/or distribution of the cancer cells in the subject.

2. The method of claim 1, the targeting agent comprising a polypeptide that specifically binds and/or complexes with the extracellular fragment.

3. The method of claim 1, the cell adhesion molecule comprising a cell surface receptor protein tyrosine phosphatase (PTP) type IIb.

4. The method of claim 1, the extracellular fragment comprising amino acid sequence of SEQ ID NO: 2 and the targeting agent comprising a polypeptide that specifically binds to and/or complexes to SEQ ID NO: 2.

5. The method of claim 1, the targeting agent comprising a polypeptide having an amino acid sequence that has at 80% sequence identity to about 10 to about 50 consecutive amino acids of SEQ ID NO: 3.

6. The method of claim 1, the targeting agent comprising a polypeptide having an amino acid sequence selected from the group consisting of SEQ ID NO: 4, SEQ ID NO: 5, SEQ ID NO: 6, SEQ ID NO: 7, and SEQ ID NO: 8.

7. The method of claim 1, the targeting agent including a polypeptide-Fc chimera, the polypeptide of the polypeptide-Fc chimera specifically binding to the extracellular fragment.

8. The method of claim 7, the polypeptide of the polypeptide-Fc chimera comprising an amino acid sequence selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

9. The method of claim 7, the Fc portion of the polypeptide-Fc chimera comprising an amino acid sequence of SEQ ID NO: 9.

10. The method of claim 7, wherein the polypeptide-Fc chimera comprises a linking molecule which is not a contiguous portion of either the polypeptide or Fc and which covalently joins an amino acid of the polypeptide to an amino acid of Fc.

11. The method of claim 1, the detectable moiety being detected by at least one of gamma imaging, positron emission tomography (PET) imaging, computer tomography (CT) imaging, magnetic resonance imaging, near infrared imaging, or fluorescent imaging.

12. The method of claim 1, the cancer cell comprising at least one of a glioma, lung cancer, melanoma, breast cancer, or prostate cancer cell.

13. The method of claim 1, the amount of the molecular probe being administered systemically to the subject.

14. The method of claim 1, the amount of the molecular probe being administered by intravenous injection to the subject.

15. The method of claim 1, the molecular probes being detected to define a tumor margin in a subject.

* * * * *

```
                        SEQUENCE LISTING

<160> NUMBER OF SEQ ID NOS: 10

<210> SEQ ID NO 1
<211> LENGTH: 1465
<212> TYPE: PRT
<213> ORGANISM: Homo sapiens

<400> SEQUENCE: 1

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240
```

```
Phe Ile Ala Ser Phe Asn Val Val Asn Thr Thr Lys Arg Asp Ala Gly
                245                 250                 255

Lys Tyr Arg Cys Met Ile Arg Thr Glu Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Val Arg Glu Glu
            420                 425                 430

Val Ser Trp Asp Thr Glu Asn Ser His Pro Gln His Thr Ile Thr Asn
        435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
            500                 505                 510

Ile Thr Leu Tyr Glu Ile Thr Tyr Lys Ala Val Ser Ser Phe Asp Pro
        515                 520                 525

Glu Ile Asp Leu Ser Asn Gln Ser Gly Arg Val Ser Lys Leu Gly Asn
    530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
            580                 585                 590

Leu Glu Thr Pro Leu Asn Gln Thr Asp Asn Thr Val Thr Val Met Leu
        595                 600                 605

Lys Pro Ala His Ser Arg Gly Ala Pro Val Ser Val Tyr Gln Ile Val
    610                 615                 620

Val Glu Glu Glu Arg Pro Arg Arg Thr Lys Lys Thr Thr Glu Ile Leu
625                 630                 635                 640

Lys Cys Tyr Pro Val Pro Ile His Phe Gln Asn Ala Ser Leu Leu Asn
                645                 650                 655

Ser Gln Tyr Tyr Phe Ala Ala Glu Phe Pro Ala Asp Ser Leu Gln Ala
```

```
                  660                 665                 670
Ala Gln Pro Phe Thr Ile Gly Asp Asn Lys Thr Tyr Asn Gly Tyr Trp
            675                 680                 685

Asn Thr Pro Leu Leu Pro Tyr Lys Ser Tyr Arg Ile Tyr Phe Gln Ala
        690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
                725                 730                 735

Thr Asp His Thr Val Lys Ile Ala Gly Val Ile Ala Gly Ile Leu Leu
            740                 745                 750

Phe Val Ile Ile Phe Leu Gly Val Val Leu Val Met Lys Lys Arg Lys
            755                 760                 765

Leu Ala Lys Lys Arg Lys Glu Thr Met Ser Ser Thr Arg Gln Glu Met
        770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
                805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Pro Phe Val Pro Thr
            835                 840                 845

Ala Ile Leu Val Pro Ile Asn Asp Glu Thr His Thr Met Ala Ser Asp
850                 855                 860

Thr Ser Ser Leu Val Gln Ser His Thr Tyr Lys Lys Arg Glu Pro Ala
865                 870                 875                 880

Asp Val Pro Tyr Gln Thr Gly Gln Leu His Pro Ala Ile Arg Val Ala
                885                 890                 895

Asp Leu Leu Gln His Ile Thr Gln Met Lys Cys Ala Glu Gly Tyr Gly
            900                 905                 910

Phe Lys Glu Glu Tyr Glu Ser Phe Phe Glu Gly Gln Ser Ala Pro Trp
        915                 920                 925

Asp Ser Ala Lys Lys Asp Glu Asn Arg Met Lys Asn Arg Tyr Gly Asn
        930                 935                 940

Ile Ile Ala Tyr Asp His Ser Arg Val Arg Leu Gln Thr Ile Glu Gly
945                 950                 955                 960

Asp Thr Asn Ser Asp Tyr Ile Asn Gly Asn Tyr Ile Asp Gly Tyr His
                965                 970                 975

Arg Pro Asn His Tyr Ile Ala Thr Gln Gly Pro Met Gln Glu Thr Ile
            980                 985                 990

Tyr Asp Phe Trp Arg Met Val Trp His Glu Asn Thr Ala Ser Ile Ile
        995                 1000                1005

Met Val Thr Asn Leu Val Glu Val Gly Arg Val Lys Cys Cys Lys
    1010                1015                1020

Tyr Trp Pro Asp Asp Thr Glu Ile Tyr Lys Asp Ile Lys Val Thr
    1025                1030                1035

Leu Ile Glu Thr Glu Leu Leu Ala Glu Tyr Val Ile Arg Thr Phe
    1040                1045                1050

Ala Val Glu Lys Arg Gly Val His Glu Ile Arg Glu Ile Arg Gln
    1055                1060                1065

Phe His Phe Thr Gly Trp Pro Asp His Gly Val Pro Tyr His Ala
    1070                1075                1080
```

-continued

```
Thr Gly Leu Leu Gly Phe Val Arg Gln Val Lys Ser Lys Ser Pro
    1085                1090                1095
Pro Ser Ala Gly Pro Leu Val Val His Cys Ser Ala Gly Ala Gly
    1100                1105                1110
Arg Thr Gly Cys Phe Ile Val Ile Asp Ile Met Leu Asp Met Ala
    1115                1120                1125
Glu Arg Glu Gly Val Val Asp Ile Tyr Asn Cys Val Arg Glu Leu
    1130                1135                1140
Arg Ser Arg Arg Val Asn Met Val Gln Thr Glu Glu Gln Tyr Val
    1145                1150                1155
Phe Ile His Asp Ala Ile Leu Glu Ala Cys Leu Cys Gly Asp Thr
    1160                1165                1170
Ser Val Pro Ala Ser Gln Val Arg Ser Leu Tyr Tyr Asp Met Asn
    1175                1180                1185
Lys Leu Asp Pro Gln Thr Asn Ser Ser Gln Ile Lys Glu Glu Phe
    1190                1195                1200
Arg Thr Leu Asn Met Val Thr Pro Thr Leu Arg Val Glu Asp Cys
    1205                1210                1215
Ser Ile Ala Leu Leu Pro Arg Asn His Glu Lys Asn Arg Cys Met
    1220                1225                1230
Asp Ile Leu Pro Pro Asp Arg Cys Leu Pro Phe Leu Ile Thr Ile
    1235                1240                1245
Asp Gly Glu Ser Ser Asn Tyr Ile Asn Ala Ala Leu Met Asp Ser
    1250                1255                1260
Tyr Lys Gln Pro Ser Ala Phe Ile Val Thr Gln His Pro Leu Pro
    1265                1270                1275
Asn Thr Val Lys Asp Phe Trp Arg Leu Val Leu Asp Tyr His Cys
    1280                1285                1290
Thr Ser Val Val Met Leu Asn Asp Val Asp Pro Ala Gln Leu Cys
    1295                1300                1305
Pro Gln Tyr Trp Leu Glu Asn Gly Val His Arg His Gly Pro Ile
    1310                1315                1320
Gln Val Glu Phe Val Ser Ala Asp Leu Glu Glu Asp Ile Ile Ser
    1325                1330                1335
Arg Ile Phe Arg Ile Tyr Asn Ala Ala Arg Pro Gln Asp Gly Tyr
    1340                1345                1350
Arg Met Val Gln Gln Phe Gln Phe Leu Gly Trp Pro Met Tyr Arg
    1355                1360                1365
Asp Thr Pro Val Ser Lys Arg Ser Phe Leu Lys Leu Ile Arg Gln
    1370                1375                1380
Val Asp Lys Trp Gln Glu Glu Tyr Asn Gly Gly Glu Gly Arg Thr
    1385                1390                1395
Val Val His Cys Leu Asn Gly Gly Gly Arg Ser Gly Thr Phe Cys
    1400                1405                1410
Ala Ile Ser Ile Val Cys Glu Met Leu Arg His Gln Arg Thr Val
    1415                1420                1425
Asp Val Phe His Ala Val Lys Thr Leu Arg Asn Asn Lys Pro Asn
    1430                1435                1440
Met Val Asp Leu Leu Asp Gln Tyr Lys Phe Cys Tyr Glu Val Ala
    1445                1450                1455
Leu Glu Tyr Leu Asn Ser Gly
    1460                1465
```

```
<210> SEQ ID NO 2
<211> LENGTH: 477
<212> TYPE: PRT
<213> ORGANISM: Homo sapiens

<400> SEQUENCE: 2

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380
```

```
Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
            420                 425                 430

Val Ser Trp Asp Thr Glu Asn Ser His Pro Gln His Thr Ile Thr Asn
        435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Ile Val Gln Thr
465                 470                 475

<210> SEQ ID NO 3
<211> LENGTH: 280
<212> TYPE: PRT
<213> ORGANISM: Homo sapiens

<400> SEQUENCE: 3

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
                20                  25                  30

Tyr Ser Thr Cys Gly Tyr Ser Gln Ser Glu Gly Asp Asp Phe Asn Trp
            35                  40                  45

Glu Gln Val Asn Thr Leu Thr Lys Pro Thr Ser Asp Pro Trp Met Pro
50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu
```

275                 280

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Glu Thr Phe Ser Gly Gly Cys Leu Phe Asp Glu Pro Tyr Ser Thr Cys
1               5                   10                  15

Gly Tyr Ser Gln
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Glu Gly Asp Asp Phe Asn Trp Glu Gln Val Asn Thr Leu Thr Lys Pro
1               5                   10                  15

Thr Ser Asp

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Thr Pro His Phe Leu Arg Ile Gln Asn Val Glu Val Asn Ala Gly Gln
1               5                   10                  15

Phe Ala Thr

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

Gly Ile Asp Val Arg Asp Ala Pro Leu Lys Glu Ile Lys Val Thr Ser
1               5                   10                  15

Ser Arg

<210> SEQ ID NO 8
<211> LENGTH: 621
<212> TYPE: PRT
<213> ORGANISM: Artificial Sequence
<220> FEATURE:
<223> OTHER INFORMATION: Synthetic Construct

<400> SEQUENCE: 8

Met Arg Thr Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

-continued

```
Tyr Ser Thr Cys Gly Tyr Ser Gln Ser Glu Gly Asp Asp Phe Asn Trp
         35                  40                  45

Glu Gln Val Asn Thr Leu Thr Lys Pro Thr Ser Asp Pro Trp Met Pro
 50                  55                  60

Ser Gly Ser Phe Met Leu Val Asn Ala Ser Gly Arg Pro Glu Gly Gln
 65                  70                  75                  80

Arg Ala His Leu Leu Leu Pro Gln Leu Lys Glu Asn Asp Thr His Cys
                 85                  90                  95

Ile Asp Phe His Tyr Phe Val Ser Lys Ser Asn Ser Pro Pro Gly
                100                 105                 110

Leu Leu Asn Val Tyr Val Lys Val Asn Asn Gly Pro Leu Gly Asn Pro
                115                 120                 125

Ile Trp Asn Ile Ser Gly Asp Pro Thr Arg Thr Trp Asn Arg Ala Glu
130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
                210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
                260                 265                 270

Tyr Ala Glu Leu Val Val Lys Glu Pro Pro Val Pro Ile Ala Pro Pro
                275                 280                 285

Gln Leu Ala Ser Val Gly Ala Thr Tyr Leu Trp Ile Gln Leu Asn Ala
290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
                355                 360                 365

Ala Leu Arg Thr Arg Thr Lys Cys Ala Asp Pro Met Arg Gly Pro Arg
370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
                420                 425                 430

Val Ser Trp Asp Thr Glu Asn Ser His Pro Gln His Thr Ile Thr Asn
435                 440                 445

Leu Ser Pro Tyr Thr Asn Val Ser Val Lys Leu Ile Leu Met Asn Pro
```

```
            450                 455                 460
Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
                500                 505                 510

Ile Thr Leu Tyr Glu Ile Thr Tyr Lys Ala Val Ser Ser Phe Asp Pro
                515                 520                 525

Glu Ile Asp Leu Ser Asn Gln Ser Gly Arg Val Ser Lys Leu Gly Asn
                530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
                580                 585                 590

Leu Glu Thr Pro Leu Asn Gln Thr Asp Asn Thr Val Thr Val Met Leu
                595                 600                 605

Lys Pro Ala His Ser Arg Gly Ala Pro Val Ser Val Tyr
                610                 615                 620

<210> SEQ ID NO 9
<211> LENGTH: 226
<212> TYPE: PRT
<213> ORGANISM: Homo sapiens

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205
```

```
His Glu Ala Leu His Asn His Tyr Thr Gln Lys Ser Leu Ser Leu Ser
    210                 215                 220
Pro Gly
225

<210> SEQ ID NO 10
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 10

Gly Phe Thr Gln Pro Glu Thr Gly Thr Asp Asn Asp Leu Trp Ser Val
1               5                   10                  15

Asp Asn Glu Lys
            20
```